(12) United States Patent
Doran et al.

(10) Patent No.: US 9,498,338 B2
(45) Date of Patent: Nov. 22, 2016

(54) METHODS FOR FORMING A CONNECTABLE INSERT

(71) Applicant: Amedica Corporation, Salt Lake City, UT (US)

(72) Inventors: Michael Doran, Emmaus, PA (US); Roy Taylor, Salt Lake City, UT (US); Peter Harris, Boca Raton, FL (US); James Ludlow, Salt Lake City, UT (US); Stephen Brown, South Jordan, UT (US)

(73) Assignee: AMEDICA CORPORATION, Salt Lake City, UT (US)

(*) Notice: Subject to any disclaimer, the term of this patent is extended or adjusted under 35 U.S.C. 154(b) by 0 days.

(21) Appl. No.: 14/515,377

(22) Filed: Oct. 15, 2014

(65) Prior Publication Data

US 2015/0026958 A1    Jan. 29, 2015

Related U.S. Application Data

(62) Division of application No. 13/666,685, filed on Nov. 1, 2012.

(60) Provisional application No. 61/554,366, filed on Nov. 1, 2011.

(51) Int. Cl.
*A61F 2/44* (2006.01)
*A61F 2/30* (2006.01)
(Continued)

(52) U.S. Cl.
CPC ............. *A61F 2/3094* (2013.01); *A61F 2/447* (2013.01); *A61F 2/4455* (2013.01); *A61F 2/4465* (2013.01); *A61F 2/4611* (2013.01);
(Continued)

(58) Field of Classification Search
CPC .............................................. A61F 2/44–2/447
USPC .......................................... 623/17.11–17.16
See application file for complete search history.

(56) References Cited

U.S. PATENT DOCUMENTS 6,423,095 B1    7/2002  Van Hoeck et al.
6,979,353 B2 *  12/2005 Bresina ...................... 623/17.16
(Continued)

FOREIGN PATENT DOCUMENTS

JP    1984-093847 U    5/1984
JP    1991-256256 A    11/1991
(Continued)

OTHER PUBLICATIONS

Office Action—U.S. Appl. No. 13/666,685, Apr. 8, 2016 (16 pgs).
(Continued)

*Primary Examiner* — Eduardo C Robert
*Assistant Examiner* — Michelle C Eckman
(74) *Attorney, Agent, or Firm* — Phillips Ryther & Winchester; Matthew D. Thayne

(57) ABSTRACT

Methods for forming an insert, such as a threaded or threadable insert, within a cavity in an implant, such as a spinal spacer. In some implementations, an implant body comprising a first, non-threadable, may be provided. A cavity may be formed in the implant body, after which an insert may be positioned within the cavity. Preferably, the insert comprises a second material distinct from the first material, wherein the second material has physical properties distinct from the first material. A female thread may then be formed within the insert, which may allow for threading an otherwise unthreadable, or relatively unthreadable, material.

13 Claims, 17 Drawing Sheets

(51) Int. Cl.
*A61F 2/46* (2006.01)
*A61F 2/28* (2006.01)

(52) U.S. Cl.
CPC *A61F2002/2817* (2013.01); *A61F 2002/2835* (2013.01); *A61F 2002/3097* (2013.01); *A61F 2002/30299* (2013.01); *A61F 2002/30331* (2013.01); *A61F 2002/30375* (2013.01); *A61F 2002/30436* (2013.01); *A61F 2002/30441* (2013.01); *A61F 2002/30448* (2013.01); *A61F 2002/30693* (2013.01); *A61F 2002/30772* (2013.01); *A61F 2002/30777* (2013.01); *A61F 2002/30779* (2013.01); *A61F 2002/30782* (2013.01); *A61F 2002/30784* (2013.01); *A61F 2002/30787* (2013.01); *A61F 2002/30797* (2013.01); *A61F 2002/30813* (2013.01); *A61F 2002/30919* (2013.01); *A61F 2002/30924* (2013.01); *A61F 2002/30925* (2013.01); *A61F 2002/4475* (2013.01); *A61F 2002/4629* (2013.01); *A61F 2310/00023* (2013.01); *A61F 2310/00047* (2013.01); *A61F 2310/00179* (2013.01); *A61F 2310/00317* (2013.01); *A61F 2310/00329* (2013.01); *Y10T 29/4998* (2015.01); *Y10T 29/49993* (2015.01); *Y10T 29/49995* (2015.01)

(56) References Cited

U.S. PATENT DOCUMENTS

| | | | |
|---|---|---|---|
| 7,060,096 B1* | 6/2006 | Schopf et al. | 623/17.11 |
| 7,235,082 B2* | 6/2007 | Bartish et al. | 606/99 |
| 7,500,991 B2* | 3/2009 | Bartish et al. | 623/17.11 |
| 7,621,960 B2* | 11/2009 | Boyd et al. | 623/17.16 |
| 7,875,075 B2* | 1/2011 | Schwab | 623/17.11 |
| 7,935,148 B2* | 5/2011 | Edie et al. | 623/17.16 |
| 7,951,177 B2 | 5/2011 | Trieu et al. | |
| 7,976,579 B2* | 7/2011 | Francis | 623/17.11 |
| 7,998,212 B2* | 8/2011 | Schwab et al. | 623/17.16 |
| 8,128,700 B2 | 3/2012 | Delurio et al. | |
| 8,147,554 B2 | 4/2012 | Hansell et al. | |
| 8,241,364 B2* | 8/2012 | Hansell et al. | 623/17.16 |
| 8,252,060 B2 | 8/2012 | Hansell et al. | |
| 8,377,132 B2* | 2/2013 | Wing et al. | 623/17.15 |
| 8,409,290 B2* | 4/2013 | Zamani et al. | 623/17.16 |
| 8,496,709 B2* | 7/2013 | Schell et al. | 623/17.16 |
| 8,506,636 B2* | 8/2013 | Dye | 623/17.16 |
| 8,545,566 B2 | 10/2013 | Niemiec et al. | |
| 8,579,980 B2 | 11/2013 | DeLurio et al. | |
| 8,617,245 B2* | 12/2013 | Brett | 623/17.16 |
| 8,673,012 B2* | 3/2014 | Smith et al. | 623/17.16 |
| 8,784,493 B2* | 7/2014 | Tsuang et al. | 623/17.16 |
| 2003/0153975 A1* | 8/2003 | Byrd et al. | 623/17.11 |
| 2005/0049706 A1 | 3/2005 | Brodke et al. | |
| 2007/0213828 A1* | 9/2007 | Trieu et al. | 623/17.11 |
| 2007/0270968 A1 | 11/2007 | Baynham et al. | |
| 2008/0009880 A1* | 1/2008 | Warnick et al. | 606/99 |
| 2008/0082173 A1* | 4/2008 | Delurio et al. | 623/17.16 |
| 2008/0154373 A1 | 6/2008 | Protopsaltis et al. | |
| 2008/0215098 A1* | 9/2008 | Imwinkelried | A61C 8/0012 606/301 |
| 2008/0221694 A1* | 9/2008 | Warnick et al. | 623/17.16 |
| 2009/0276049 A1* | 11/2009 | Weiland | 623/17.16 |
| 2010/0094422 A1* | 4/2010 | Hansell et al. | 623/17.16 |
| 2010/0114105 A1 | 5/2010 | Butters et al. | |
| 2010/0161057 A1 | 6/2010 | Berry et al. | |
| 2010/0204798 A1* | 8/2010 | Gerbec et al. | 623/17.16 |
| 2010/0249935 A1* | 9/2010 | Slivka et al. | 623/17.16 |
| 2010/0256760 A1* | 10/2010 | Hansell | 623/17.11 |
| 2010/0256767 A1* | 10/2010 | Melkent | 623/17.16 |
| 2010/0305704 A1 | 12/2010 | Messerli et al. | |
| 2010/0312346 A1 | 12/2010 | Kueenzi et al. | |
| 2010/0331981 A1 | 12/2010 | Mohammed | |
| 2011/0082555 A1* | 4/2011 | Martz et al. | 623/17.16 |
| 2011/0098818 A1 | 4/2011 | Brodke et al. | |
| 2011/0106259 A1* | 5/2011 | Lindenmann et al. | 623/17.16 |
| 2011/0172776 A1* | 7/2011 | Warnick et al. | 623/17.16 |
| 2011/0178601 A1 | 7/2011 | Edie et al. | |
| 2011/0276142 A1* | 11/2011 | Niemiec et al. | 623/17.16 |
| 2012/0010715 A1 | 1/2012 | Spann | |
| 2012/0010716 A1 | 1/2012 | Spann | |
| 2012/0010717 A1* | 1/2012 | Spann | 623/17.16 |
| 2012/0130494 A1 | 5/2012 | DeLurio | |
| 2012/0165943 A1* | 6/2012 | Mangione et al. | 623/17.16 |
| 2012/0165945 A1 | 6/2012 | Hansell et al. | |
| 2012/0277866 A1* | 11/2012 | Kalluri et al. | 623/17.16 |
| 2013/0006362 A1* | 1/2013 | Biedermann et al. | 623/17.16 |
| 2013/0023937 A1* | 1/2013 | Biedermann et al. | 606/279 |
| 2013/0030531 A1* | 1/2013 | Brodke et al. | 623/17.16 |
| 2013/0030534 A1 | 1/2013 | DeLurio et al. | |
| 2013/0096685 A1* | 4/2013 | Ciupik et al. | 623/17.16 |
| 2013/0110247 A1* | 5/2013 | Doran et al. | 623/17.16 |
| 2013/0123925 A1* | 5/2013 | Patterson et al. | 623/17.16 |
| 2013/0268077 A1* | 10/2013 | You et al. | 623/17.16 |
| 2013/0302509 A1 | 11/2013 | McEntire et al. | |
| 2013/0302512 A1* | 11/2013 | McEntire et al. | 427/2.26 |
| 2014/0039626 A1* | 2/2014 | Mitchell | 623/17.16 |
| 2014/0039627 A1 | 2/2014 | Weiland | |
| 2014/0039628 A1 | 2/2014 | DeLurio et al. | |
| 2014/0052258 A1* | 2/2014 | Ball et al. | 623/17.16 |
| 2014/0058512 A1* | 2/2014 | Petersheim | 623/17.16 |
| 2014/0058513 A1* | 2/2014 | Gahman et al. | 623/17.16 |
| 2014/0058518 A1 | 2/2014 | Niemiec et al. | |
| 2014/0114414 A1* | 4/2014 | Abdou et al. | 623/17.16 |
| 2014/0114421 A1* | 4/2014 | Ullrich et al. | 623/17.16 |
| 2014/0148907 A1* | 5/2014 | Gately | 623/17.16 |
| 2014/0172107 A1* | 6/2014 | Thirugnanasambandam et al. | 623/17.16 |
| 2014/0200672 A1* | 7/2014 | Alheidt | 623/17.16 |
| 2014/0249628 A1 | 9/2014 | Weiman | |
| 2014/0249630 A1 | 9/2014 | Weiman et al. | |
| 2014/0249631 A1 | 9/2014 | Weiman | |
| 2014/0249632 A1* | 9/2014 | Weiman | 623/17.16 |

FOREIGN PATENT DOCUMENTS

| | | |
|---|---|---|
| JP | 003449415 | 7/2003 |
| JP | 2007-521881 A | 8/2007 |
| JP | 2009-504207 A | 2/2009 |
| JP | 2012-5000058 A | 1/2012 |
| WO | WO2010019799 | 2/2010 |

OTHER PUBLICATIONS

European Search Report—EU Application No. 12845350.3, Nov. 11, 2015 (6 pgs).
JP2012-5000058A—Machine Translation of Application.
JP1984-093847U—Machine Translation of Application.
JP2007-521881A—Machine Translation of Application.
JP2009-504207A—Machine Translation of Application.
JP1991-256256A—Machine Translation of Application.
JBP 003449415—Machine Translation of Application.

* cited by examiner

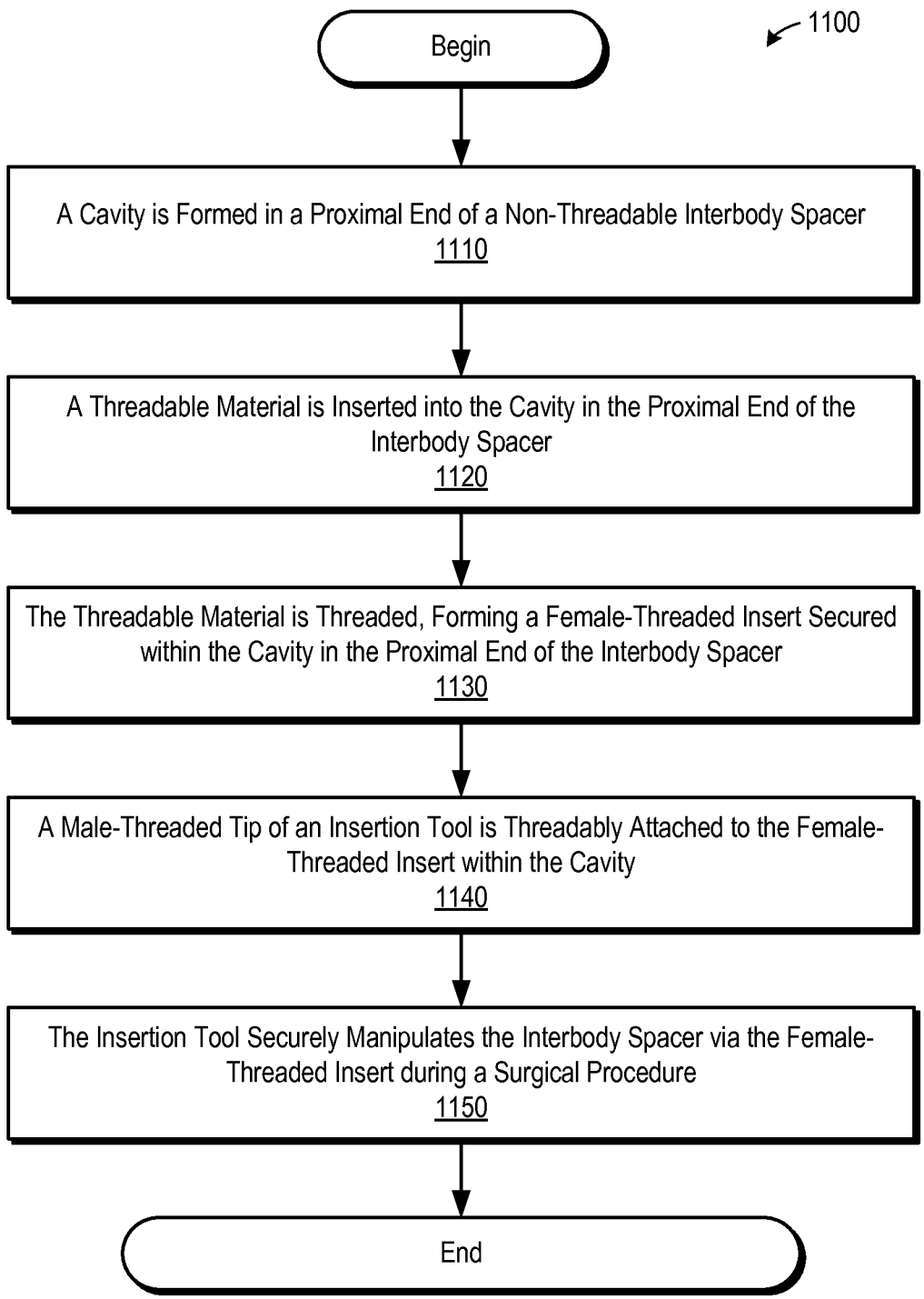

US 9,498,338 B2

METHODS FOR FORMING A CONNECTABLE INSERT

RELATED APPLICATIONS

This is a divisional application of U.S. patent application Ser. No. 13/666,685 filed on Nov. 1, 2012 and titled "IMPLANTS WITH A CONNECTABLE INSERT AND RELATED SYSTEMS AND METHODS," which claims the benefit of priority of U.S. Provisional Patent Application No. 61/554,366 filed Nov. 1, 2011 and titled "IMPLANTS WITH A CONNECTABLE INSERT AND RELATED SYSTEMS AND METHODS." Both of the aforementioned patent applications are incorporated herein by specific reference in their entireties.

TECHNICAL FIELD

This disclosure generally relates to systems and methods for performing spinal and other surgical procedures. More specifically, embodiments of the present disclosure relate to threaded surgical implants, such as interbody spacers, for interbody fusion of the spine or other bony structures.

BACKGROUND

The degeneration of the intervertebral disk, such as the degeneration of the nucleus pulpous of the disk, results in a loss of height in the affected disk space which is associated with a weakening of the annulus fibrous and of the ligaments. As a consequence, the spinal column may become instable and more susceptible to horizontal displacement of the vertebral bodies with respect to one another. Such movement may result in impairments of the nerve roots in this region and/or of the spinal marrow with pain resulting therefrom.

The principle treatment of these symptoms consists of the surgical removal of the nucleus pulpous and the insertion of support bodies in order to restore the normal height of the disk space. While there are a number of traditional systems and methods for inserting support bodies, there are a variety of demands on both the surgeon performing an intervertebral disk procedure, the tools used to secure and insert the interbody spacers, and on the spinal spacers themselves.

In many cases, a surgeon inserts an interbody spacer within a spinal column using an insertion tool configured to threadably secure an interbody spacer. Many insertion tools include a male-threaded tip configured to mate with a corresponding female-threaded component formed in or on an interbody spacer. Alternatively, an insertion tool may be configured to grasp the perimeter of an interbody spacer during insertion.

Traditional interbody spacers, such as fusion cages, may comprise bodies manufactured from PEEK (polyehteretherketone). PEEK is commonly used because it does not distort MRI and CT images of the vertebrae. However, because new bone growth does not adhere well to PEEK, bone fusion with a PEEK cage typically relies on bridging bone growth through holes in the cage to provide stabilization.

The reliance on bridged bone growth through holes in the cage leads to interbody spacers with a large percentage of open space relative to the supporting PEEK structure. The more open space an interbody spacer has, the higher the load on each portion of the interbody spacer will be. In order to increase the strength of the interbody spacer, increase the stiffness of the interbody spacer, and/or to foster bone growth, various alternative materials have been developed for use in interbody spacers.

Interbody spacers made of PEEK can be readily threaded in order to accommodate insertion tools with male-threaded members. However, some materials that are suitable for interbody spacers, such as silicon nitride ($Si_3N_4$) and various other ceramics that are otherwise viable materials for use as spinal implants, are either not threadable, not easily threaded, or result in threads that break under a load.

SUMMARY

The present disclosure provides apparatus, systems, and methods for forming an insert or another similar connection feature into a spacer or other implant that is made up of a material having different characteristics from the primary material of the implant. For example, the implant may be not threadable, not easily threaded, or may result in weak or otherwise undesirable threads or other connection features, and a female-threaded or threadable insert may be secured within the implant to improve the ability of the implant to provide a suitably strong set of threads, such as for engagement with an installation instrument.

According to some implementations, a cavity may be drilled or otherwise formed in a non-threadable interbody spacer. The cavity may then be filled, or otherwise receive, a threadable material, such as PEEK, polypropylene, titanium, or another metal. The threadable material may then be threaded in order to form a female-threaded member within the non-threadable interbody spacer.

According to one implementation, a silicon nitride interbody spacer may have a cavity formed in a proximal end. The cavity may be round, oval, rectangular, polygonal, or another shape. The cavity may be tapered and may include one or more vents, retention features, or anti-rotational features. A threadable material, such as PEEK, polypropylene, polyethylene, polymethylene, or another plastic, acrylate, acrylics, titanium, or another metal, may be press-fit, injection molded, extruded, adhered, or melted into the cavity. The threadable material may then be threaded using a threading tool to create a female-threaded insert within the interbody spacer. A male-threaded insertion tool may threadably secure the non-threadable interbody spacer via the female-threaded insert during surgical insertion.

According to various alternative embodiments and implementations, an insert may be formed in any interbody spacer made from any of a variety of materials. Moreover, such an insert may be formed in other biomedical implants, medical devices, support members, and/or structures that are otherwise non-threadable or not capable of forming a similar connection feature of suitable strength. For example, a female-threaded insert or another insert having distinct physical properties from one or more other materials making up the device may be formed in intervertebral spacers, spinal plates, bridge members, bone screws, facet clamps, and/or other medical support or fastening members.

Some embodiments of biomedical implants according to the present disclosure may comprise a body comprising a first material and an insert coupled with the body. The biomedical implant may comprise, for example, a spinal interbody spacer. The insert may comprise a second material distinct from the first material, and the second material may have physical properties distinct from the first material. For example, the second material may be threadable and the first material may be non-threadable. In some embodiments, the second material may comprise, for example, PEEK, polypropylene, polyethylene, polymethylene, acrylate, acrylic, and titanium. The first material may comprise, for example, a silicon nitride ceramic or another sinterable material.

A connectable feature may be formed within the insert such that the insert is capable of being connected with a device, such as a surgical instrument. The connectable feature may comprise a female thread formed within the insert. In such embodiments, the female thread may be configured to be connected with an insertion tool for installing the interbody spacer during surgery. The insert may be positioned within a cavity of the implant. In some embodiments, the cavity may comprise a thru-bore. The cavity may comprise a wide-base cavity configured to prevent the insert from being removed from the cavity. The insert may comprise an anti-rotation feature and/or a retention feature. In some embodiments, the anti-rotation feature may also comprise a retention feature.

In one more specific embodiment according to the present disclosure, a spinal interbody spacer system may comprise an interbody spacer comprising a silicon nitride ceramic material. A cavity may be formed within the interbody spacer with a threaded insert positioned within the cavity. The threaded insert may comprise a threadable material distinct from the silicon nitride ceramic material. The threaded insert may also comprise a retention feature configured to prevent the threaded insert from being removed from the cavity. An insertion tool comprising a male thread configured to engage the threaded insert may also be provided. In some embodiments the interbody spacer may comprise a STALIF implant.

In some implementations of methods for forming a connectable insert within a biomedical implant, the method may comprise providing an implant body comprising a first material, wherein the first material is non-threadable, forming a cavity in the implant body, and positioning an insert within the cavity. The insert may comprise a second material distinct from the first material, and the second material may have physical properties distinct from the first material. A female thread may be formed within the insert.

In some embodiments, the spinal spacer may comprise a concave face and an opposite convex face. A first end wall may connect the concave face with the convex face and an opposite second end wall may connect the concave face with the convex face. The cavity may be positioned within at least one of the first and second end walls.

In some implementations, the step of positioning an insert within the cavity may comprise at least one of press-fitting, injection molding, extruding, and melting the second material into the cavity. In some implementations, the step of forming a cavity in the implant body may comprise forming a wide-base cavity configured to prevent the insert from being removed from the cavity. An anti-rotation feature may also be formed on the insert. In some implementations, the step of forming an anti-rotation feature on the insert may comprise forming an anti-rotation cavity that is coupled with the cavity.

In some implementations, the step of positioning an insert within the cavity may comprise providing a block of threadable material having a V-shaped nose and forcing the block of threadable material into the cavity such that the V-shaped nose enters the cavity first. The step of positioning an insert within the cavity may also comprise heating the second material in order to increase the malleability of the second material. The step of positioning an insert within the cavity may also comprise providing a guide structure comprising a center hole and an engagement surface configured with a shape corresponding to a surface of the implant body surrounding the cavity and pressing the second material into the cavity through the guide structure.

Additional aspects of the various apparatus, systems, and methods will be apparent from the following detailed description, which proceeds with reference to the accompanying drawings.

BRIEF DESCRIPTION OF THE DRAWINGS

Non-limiting and non-exhaustive embodiments of the disclosure are described, including various embodiments of the disclosure with reference to the figures, in which:

FIG. 11 is a flow chart of one method for forming a female-threaded insert within a proximal end of an interbody spacer.

DETAILED DESCRIPTION

Figure 1A:
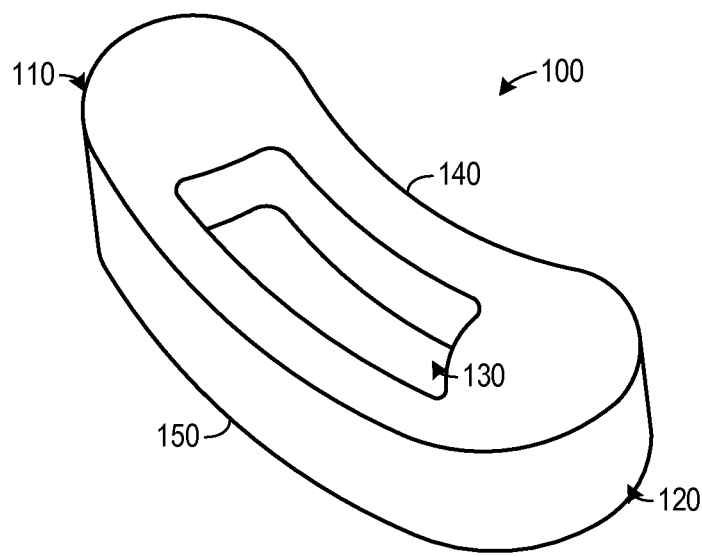
FIG. 1A is a perspective view of an exemplary interbody spacer, including a center cutout to facilitate bone fusion.

In the following description, numerous specific details are provided for a thorough understanding of the various embodiments disclosed herein. The systems and methods disclosed herein can be practiced without one or more of the specific details, or with other methods, components, materials, etc. In addition, in some cases, well-known structures, materials, or operations may not be shown or described in detail in order to avoid obscuring aspects of the disclosure. Furthermore, the described features, structures, or characteristics may be combined in any suitable manner in one or more alternative embodiments.

The present disclosure describes examples of apparatus, systems, and methods for forming an insert within a cavity in an implant formed from one or more materials having distinct physical properties from the insert. For example, an insert made from a material that is easily threadable may be positioned on, or within, an implant formed from a generally non-threadable material. More generally, an insert comprising a material that is desirable or suitable for forming a particular connection feature may be positioned on, or within, an implant made from a material that is generally unsuitable for forming a particular desired connection feature.

According to various embodiments, an interbody spacer may include a proximal end and a distal end. The interbody spacer may be manufactured using a non-threadable material, such as a silicon nitride ceramic, another ceramic material, a glass material, or a highly porous material. A cavity may be formed in the interbody spacer, such as in the proximal end for example. A threadable material may be inserted into the cavity. The threadable material may then be threaded in order to form a female-threaded insert within the non-threadable interbody spacer. An insertion tool configured with a male-threaded tip may then be used to threadably secure the interbody spacer via the female-threaded insert during surgery. In other embodiments, the insert(s) may be configured with larger threads to receive, for example, a bone screw, such as in a standalone anterior lumbar interbody fusion ("STALIF") implant.

In some embodiments of a spacer comprising a silicon nitride ceramic, the silicon nitride ceramic may comprise a doped silicon nitride ceramic. Examples of suitable silicon nitride materials are described in, for example, U.S. Pat. No. 6,881,229, titled "Metal-Ceramic Composite Articulation," which is incorporated by reference herein. In some embodiments, dopants such as alumina ($Al_2O_3$), yttria ($Y_2O_3$), magnesium oxide, and/or strontium oxide, can be processed to form a doped composition of silicon nitride. In embodiments comprising a doped silicon nitride or another similar ceramic material, the dopant amount may be optimized to achieve the highest density, mechanical, and/or antibacterial properties. In further embodiments, the biocompatible ceramic may have a flexural strength greater than about 900 MPa, and a toughness greater than about 9 MPa·m$^{1/2}$. Flexural strength can be measured on standard 3-point bend specimens per American Society for Testing of Metals (ASTM) protocol method C-1161, and fracture toughness can be measured using single edge notched beam specimens per ASTM protocol method E399. In some embodiments, powders of silicon nitride may be used to form the ceramic implants, either alone or in combination with one or more of the dopants referenced above.

Other examples of suitable silicon nitride materials are described in U.S. Pat. No. 7,666,229 titled "Ceramic-Ceramic Articulation Surface Implants," which is also hereby incorporated by reference. Still other examples of suitable silicon nitride materials are described in U.S. Pat. No. 7,695,521 titled "Hip Prosthesis with Monoblock Ceramic Acetabular Cup," which is also hereby incorporated by reference.

According to various embodiments, the cavity may be shaped to reduce or prevent the rotation or separation of the threadable material from the non-threadable interbody spacer. For example, the cavity may be rectangular, oval, hexagonal, octagonal, polygonal, and/or other non-circular shape. Additionally, the cavity may be tapered, may include an anti-rotation forming feature, and/or may include a vent. The cavity may be formed during the initial manufacturing process, or may be formed later in a post-processing phase, such as through the use of mechanical drilling, chemical etching, laser etching, particle blasting, and/or other cavity-forming process.

The material inserted into the cavity may comprise PEEK (polyehteretherketone), a polypropylene, titanium, metals, alloys, and/or other materials having desirable characteristics not present in the material within which it is placed. For example, the material may be capable of being threaded or may be capable of forming more rigid or otherwise more desirable threads than the primary material or materials of the spacer. The threadable material may be inserted within the cavity using any of a wide variety of insertion processes, including, but not limited to press-fitting, injection molding, extrusion, adhesives, or melting. According to some embodiments, a combination of insertion processes may be utilized. For example, a PEEK material may be injected into the cavity and then further pressed to finalize the insertion.

The threadable material may then be threaded, thereby forming a female-threaded insert within the cavity. Alternatively, a material may be inserted into the cavity that is configured to provide some other type of support. For example, a material may be inserted within one or more cavities formed in an interbody spacer in order to provide structural support for supporting, for example, bone screws in a STALIF implant, interact with various medical support and manipulation devices, interact with insertion tools, and/or to provide a contact point. For instance, certain ceramic interbody spacers may be prone to fracturing under a point load. Accordingly, a cavity may be formed at an anticipated location of a point load and the cavity may be filled with a second material capable of supporting the point load. The second material need not necessarily be threadable.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this disclosure are not necessarily all referring to the same embodiment. In particular, an "embodiment" may be a system, an article of manufacture, a method, or a product of a process.

The phrases "non-threadable" and similar terms used herein need not encompass only materials that are impossible or impractical to thread. Rather, "non-threadable" is intended to encompass materials that are not readily threadable, not easily threadable, and/or materials which when threaded result in weak or otherwise unsuitable threads. Accordingly, a "non-threadable material," as used herein, may in fact be threadable through difficult, expensive, or cumbersome processes. Moreover, a "non-threadable material," as used herein may in fact be threadable, but the threads may be unsuitable for a particular purpose (e.g., the threads may easily strip, break, bend, and/or otherwise fail to support an adequate load). Examples of "non-threadable" materials include, but are not limited to, ceramics, such as silicon nitride ceramics, and glass materials.

Some of the infrastructure and manufacturing tools and/or machinery that can be used with embodiments disclosed herein are already available, such as extruders, presses, injectors, interbody spacers, interbody spacers, threading tools, and threading machines. The interbody spacers of some embodiments may be used as intervertebral spacers or interspinous spacers, and may also be used with a posterior stabilization system, and dynamic rod stabilization system. Any variety of insertion tools and insertion techniques may be utilized in conjunction with various embodiments, including, but not limited to, STALIF, PLIF, and TLIF approaches.

The components of the embodiments, as generally described and illustrated in the figures herein, could be arranged and designed in a wide variety of different configurations. In other instances, well-known structures associated with interbody fusion have not been shown or described in detail to avoid unnecessarily obscuring descriptions of the present exemplary embodiments. In addition, the steps of the described methods do not necessarily need to be executed in any specific order, or even sequentially, nor need the steps be executed only once, unless otherwise specified. For example, some of the steps in exemplary methods disclosed herein may, in some implementations, be performed simultaneously.

The embodiments of the disclosure are best understood by reference to the drawings, wherein like parts are designated by like numerals throughout. In the following description, numerous details are provided to give a thorough understanding of various embodiments. However, the embodiments disclosed herein can be practiced without one or more of the specific details, or with other methods, components, materials, etc. In other instances, well-known structures, materials, or operations are not shown or described in detail to avoid obscuring aspects of this disclosure.

FIG. 1A is a perspective view of an interbody spacer 100. Interbody spacer 100 may be manufactured using a non-threadable material, such as a silicon nitride ceramic or another ceramic, and may have an arcuate, rocker-like shape with a concave anterior face 140 and a convex posterior face 150. Interbody spacer 100 may include one or more holes, thru-bores, apertures, or hallows, such as aperture 130. According to various embodiments, interbody spacer 100 may have a proximal end 110 and a distal end 120. Distal end 120 may be the leading edge during insertion, with proximal end 110 being closest to a surgeon. Alternatively, interbody spacer 100 may be surgically inserted in any alternative orientation.

Figure 1B:
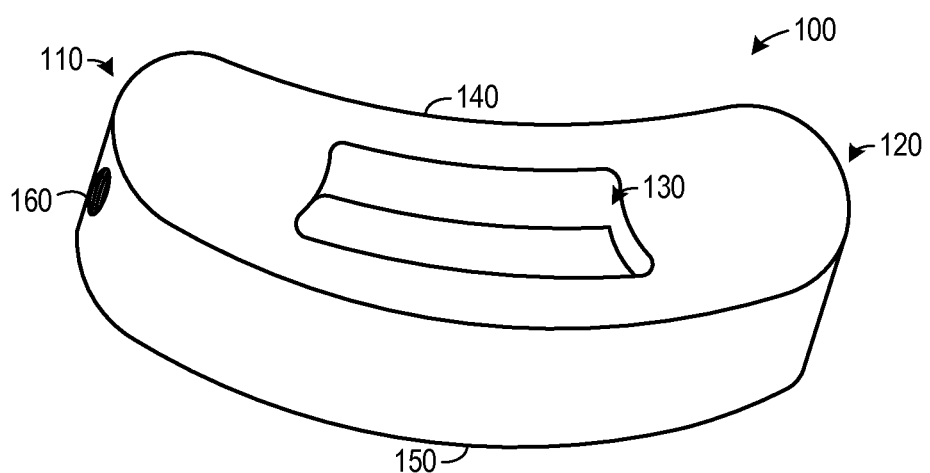
FIG. 1B is a perspective view of the interbody spacer, including a female-threaded insert configured to receive a male-threaded tip of an insertion tool.
Figure 1C:
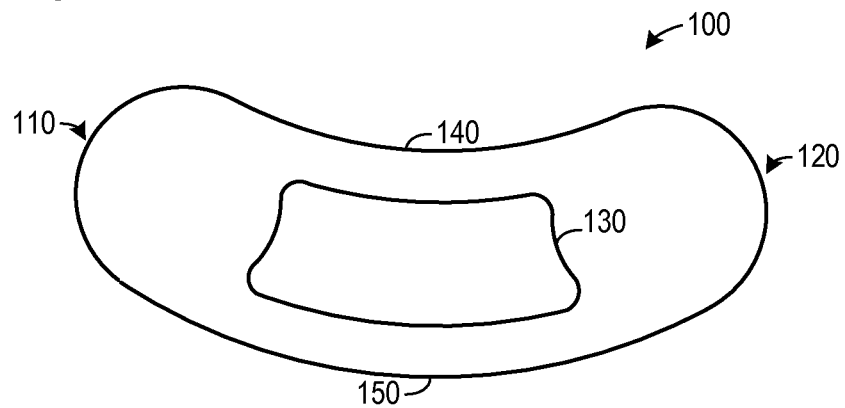
FIG. 1C is a side view of the interbody spacer.

FIG. 1B is another perspective view of interbody spacer 100 including a female-threaded insert 160 configured to receive a male-threaded tip of an insertion tool. As illustrated, female-threaded insert 160 may be located on proximal end 110 of interbody spacer 100. Alternatively, any number of female-threaded inserts 160 or other inserts may be positioned at various locations on interbody spacer 100. For example, one or more female-threaded inserts (or other inserts) may be positioned on distal end 120, anterior face 140, posterior face 150, the top surface, and/or the bottom surface. FIG. 1C provides a side view of interbody spacer 100, including proximal end 110, distal end 120, anterior face 140, and posterior face 150.

Figure 2A:
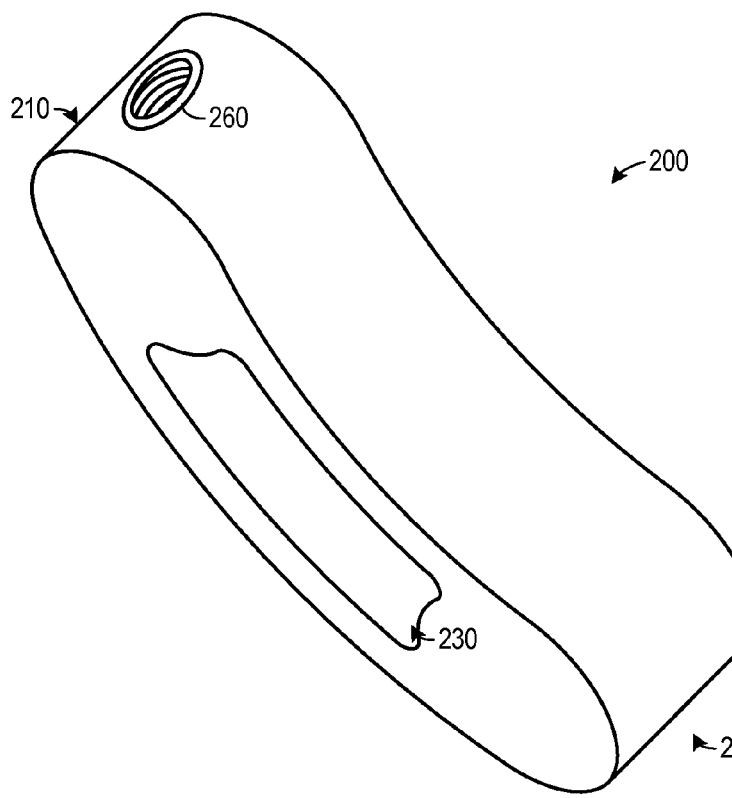
FIG. 2A is a perspective view of an exemplary interbody spacer, including a round, female-threaded insert configured to receive a male-threaded tip of an insertion tool.

FIG. 2A is a perspective view of an alternative embodiment of an interbody spacer 200. Interbody spacer 200 includes a round, female-threaded insert 260 positioned on a proximal end 210 of interbody spacer 200. A threaded male tip of an insertion tool may threadably secure female-threaded insert 260 during surgical insertion of interbody spacer 200. The insertion tool may then guide distal end 220 of interbody spacer 200 as a leading edge during surgical insertion. Aperture 230 may serve as a location for bone morphogenic proteins (BMPs).

Figure 2B:
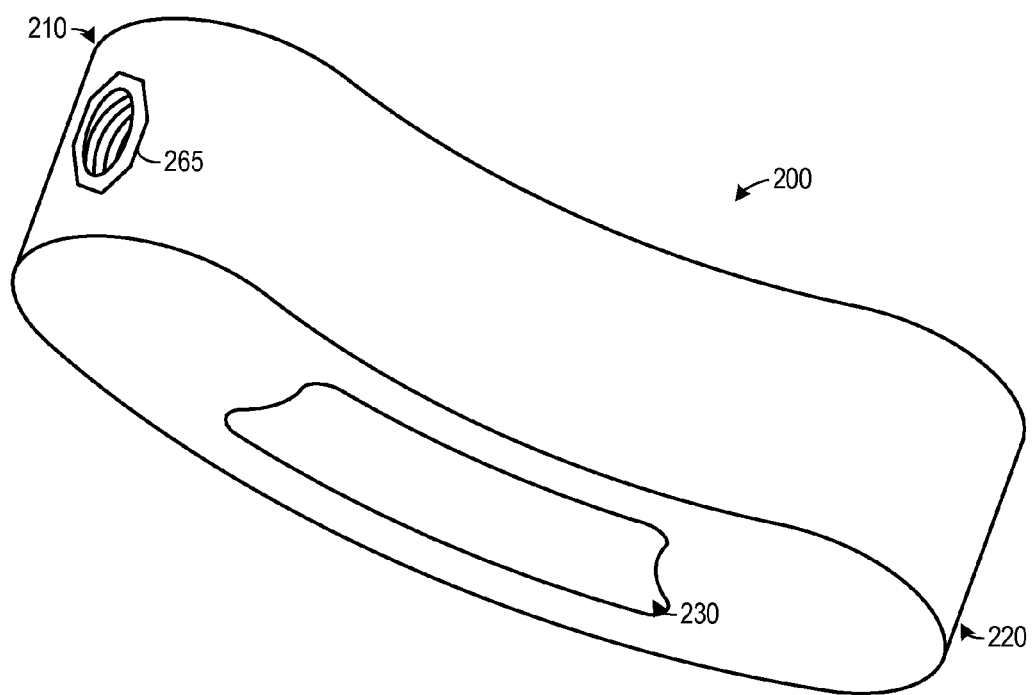
FIG. 2B is a perspective view of the interbody spacer, including an octagonal, female-threaded insert configured to receive a male-threaded tip of an insertion tool.

FIG. 2B is another perspective view of interbody spacer 200, including an octagonal, female-threaded insert 265 configured to receive a male-threaded tip of an insertion tool. According to various embodiments, an octagonal cavity may be formed in proximal end 210 of non-threadable interbody spacer 200. A threadable material may then be inserted within the octagonal cavity. The threadable material may then be threaded in order to form female-threaded insert 265. The octagonal shape of female-threaded insert 265 may reduce the likelihood of female-threaded insert 265 rotating within the cavity. That is, the potential for the threadable material separating and rotating within the cavity is reduced by inserting the threadable material into a cavity having a shape other than circular.

Insert 265 therefore comprises an anti-rotation feature, in that the shape of insert 265 prevents the insert from being rotated within its corresponding cavity. However, insert 265 does not necessarily also comprise a retention feature (although a separate retention feature may be provided if desired), since the octagonal shape itself need not necessarily prevent insert 265 from being removed from its cavity. However, as will be apparent after reviewing this disclosure as a whole, some anti-rotation features may also comprise retention features if such features both inhibit rotation and help prevent the insert from being removed from a cavity.

Figure 3A:
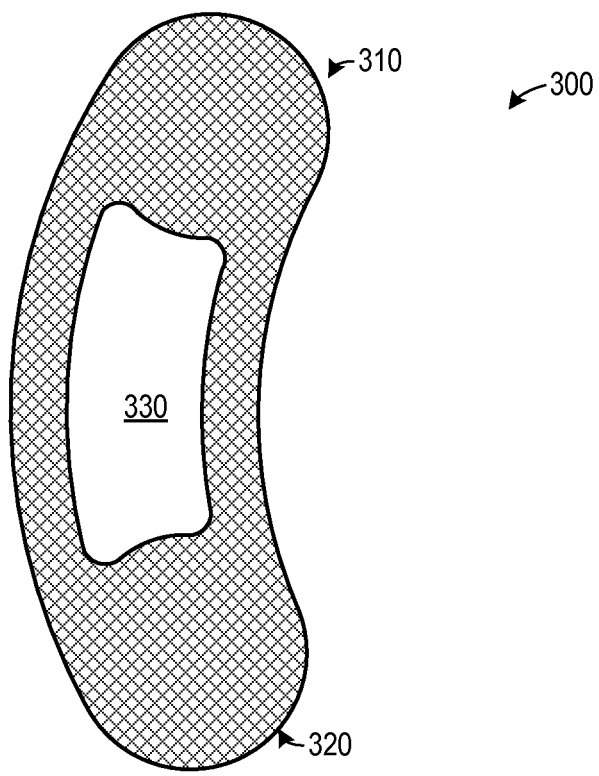
FIG. 3A is a cross-sectional view of an exemplary interbody spacer manufactured using a non-threadable material.
Figure 3B:
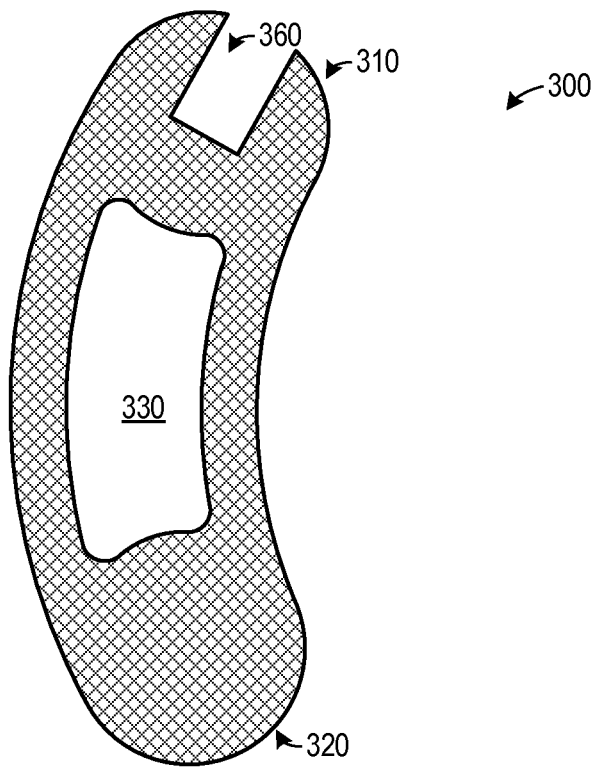
FIG. 3B is a cross-sectional view of the non-threadable interbody spacer with a cavity formed in a proximal end.

FIG. 3A is a cross-sectional view of an interbody spacer 300 manufactured using a non-threadable material. For example, interbody spacer 300 may be manufactured using a silicon nitride ceramic, another ceramic, or a related composite material. Interbody spacer 300 may include a distal end 320, a proximal end 310 and an aperture 330. As illustrated in FIG. 3B, a cavity 360 may be formed in proximal end 310 of interbody spacer 300.

Cavity 360 may be formed having any shape, width, length, depth, and/or a tapered configuration. Moreover, any of a wide variety of retention features and/or anti-rotational features may be formed by extending portions of cavity 360. Additionally, any number of cavities may be formed in interbody spacer 300 and may be positioned in various locations in addition to, or as an alternative to, proximal end 310. Cavity 360 may be formed by drilling, chemical etching, laser etching, particle blasting, and/or though other material-removing processes.

Alternatively, a cavity may be formed in interbody spacer 300 during the manufacturing stage, such as through the use of molds configured to provide a cavity. In other words, a cavity may be formed in a silicon nitride ceramic or other material for sintering during a green state, instead of machining the cavity after firing. Such embodiments may eliminate the need to remove material and/or reduce the amount of material that needs to be removed in order to form an adequate cavity.

Figure 3C:
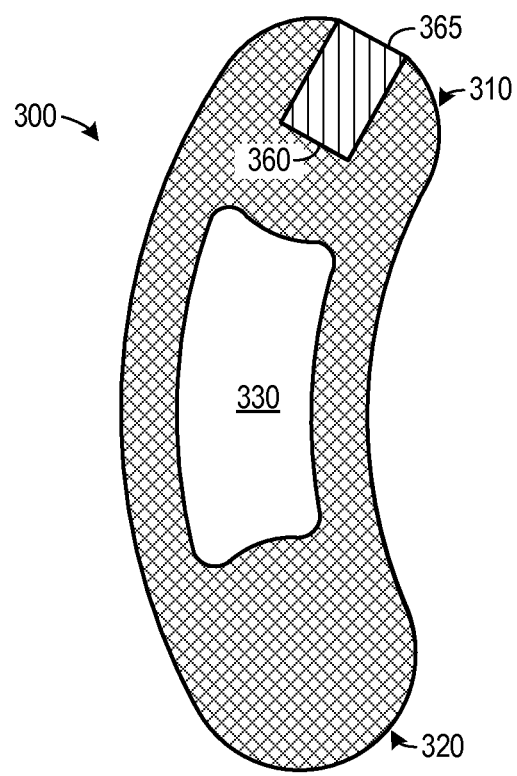
FIG. 3C is a cross-sectional view of the non-threadable interbody spacer with a threadable material inserted into the cavity.

As illustrated in FIG. 3C, a threadable material 365 may be inserted into cavity 360. Threadable material 365 may be configured to substantially fill cavity 360. Threadable material 365 may comprise PEEK, a polypropylene, titanium, aluminum, another metal, an alloy, an epoxy, and/or any other material capable of being threaded. Threadable material 365 may be inserted into cavity 360 using any of a wide variety of insertion processes, including, but not limited to press-fitting, injection molding, extrusion, adhesives, or melting. Excess material 365 that may overflow cavity 360 may be sanded smooth or otherwise removed, such that the surface of threadable material 365 is even with the surface of interbody spacer 300, as illustrated in FIG. 3C.

Figure 3D:
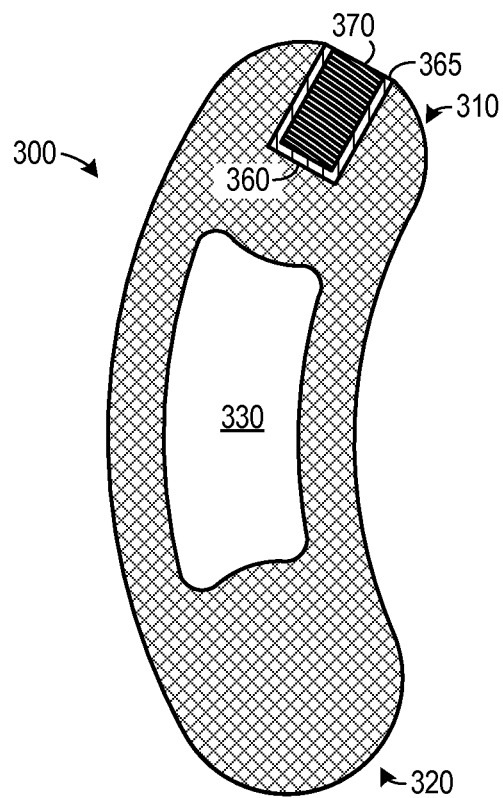
FIG. 3D is a cross-sectional view of a non-threadable interbody spacer with threads formed in the threadable material inserted within the cavity.

FIG. 3D illustrates a cross-sectional view of interbody spacer 300 after threadable material 365 has been threaded to form female-threaded insert 370. Female-threaded insert 370 may be configured to mate with a male-threaded insertion tool or with fixation members, such as screws, bolts, rods, and the like. Accordingly, a non-threadable interbody spacer 300 may be configured with a female-threaded insert 370, such that the non-threadable interbody spacer may be threadably secured by an insertion tool.

Figure 4A:
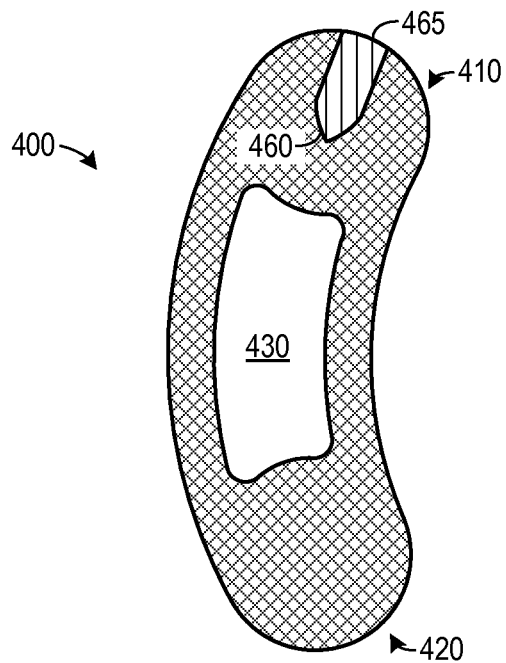
FIG. 4A is a cross-sectional view of an exemplary non-threadable interbody spacer with a threadable material inserted within a tapered cavity in a proximal end of the interbody spacer.

FIG. 4A illustrates another embodiment of a non-threadable interbody spacer 400 with a threadable material 465 inserted within a tapered cavity 460 formed in a proximal end 410 of interbody spacer 400. Interbody spacer 400 is illustrated as having an arcuate shape with a proximal end 410, a distal end 420, and an aperture 430. However, the shape, size, and dimensions of interbody spacer 400 may be adapted or modified for a particular application.

In the illustrated embodiment, tapered cavity 460 is wider near proximal end 410 of interbody spacer 400 and is narrower towards distal end 420 of interbody spacer 400. In alternative embodiments, tapered cavity 460 may be wider near distal end 420 of interbody spacer 400 and narrower near proximal end 410 of interbody spacer 400.

Figure 4B:
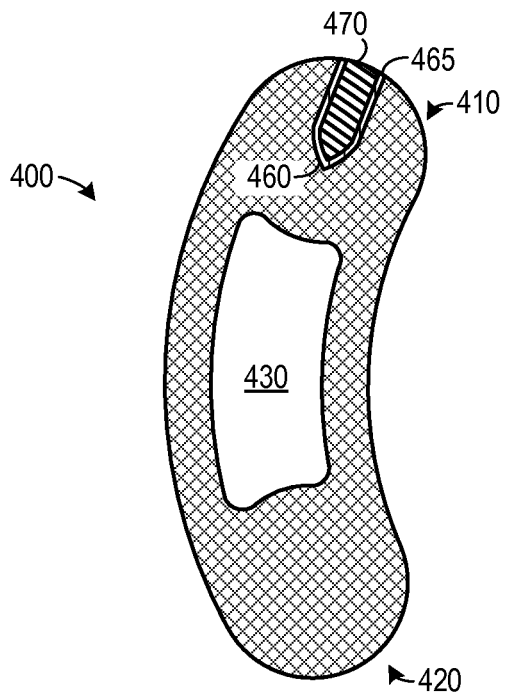
FIG. 4B is a cross-sectional view of the non-threadable interbody spacer with threads formed in the threadable material inserted within the tapered cavity.

As illustrated in FIG. 4B, threadable material 465 may be threaded in order to form a female-threaded insert 470 within cavity 460. The size and shape of the threads may be adapted for compatibility with various insertion tools and/or fasteners.

Figure 5A:
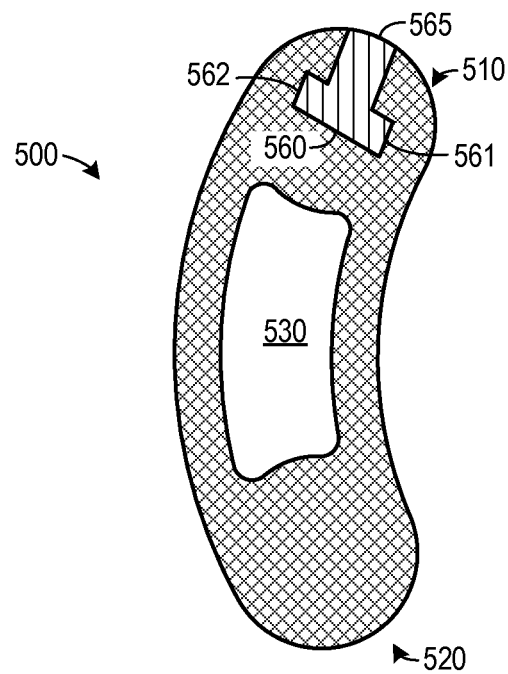
FIG. 5A is a cross-sectional view of an exemplary non-threadable interbody spacer with a threadable material inserted within a wide-base cavity in a proximal end of the interbody spacer.

FIG. 5A illustrates another embodiment of a non-threadable interbody spacer 500 with a threadable material 565 inserted within a wide-base cavity 560 in a proximal end 510 of interbody spacer 500. Wide-base cavity 560 may be used to form a retention feature in the opposing ends of the insert formed by the cavity that may provide stability and help prevent the implant from being removed from and/or rotated within, the spacer, as explained in greater detail below.

As illustrated in the figure, wide-base cavity 560 may include extended cavity regions 561 and 562 towards the distal end 520 of interbody spacer 500. Accordingly, the opening of wide-base cavity 560 near proximal end 510 of interbody spacer 500 may be substantially narrower than the base of wide-base cavity 560. Wide-base cavity 560 may provide an advantage in that threadable material 565 cannot be easily removed from cavity 560 once threadable material 565 has solidified or otherwise become secured within wide-base cavity 560.

Threadable material 565 may be melted, press-fit, or injected within wide-base cavity 560. Once fully cured, solidified, and/or otherwise secured within wide-base cavity 560, extended cavities 561 and 562 may prevent the removal of threadable material 565. Moreover, depending on the shape of extended cavity regions 561 and 562, they may additionally serve as anti-rotational features preventing or reducing the likelihood of threadable material 565 rotating within wide-base cavity 560.

Figure 5B:
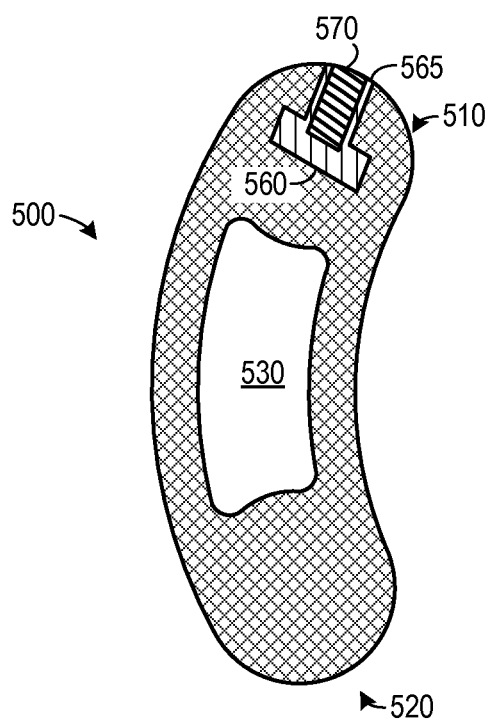
FIG. 5B is a cross-sectional view of the non-threadable interbody spacer with threads formed in the threadable material inserted within the wide-base cavity.

Threadable material 565 may be threaded in order to form a female-threaded insert 570 within wide-base cavity 560, as illustrated in FIG. 5B. Any of a wide variety of insertion tools and/or fasteners may then be threadably secured to female-threaded insert 570. An insertion tool may threadably secure interbody spacer 500 during surgical insertion via female-threaded insert 570.

As previously described, aperture 530 may serve as a delivery mechanism for BMP and/or provide a location for additional bone growth. Interbody spacer 500 may comprise, for example, a non-threadable silicon nitride or other ceramic, glass, and/or other non-threadable material. Threadable material 565 may comprise, for example, PEEK, a polypropylene, titanium, aluminum, other metal, an alloy, an epoxy, and/or other material capable of being threaded, or at least more suitable for desirable thread formation than the material(s) making up spacer 500.

Figure 6A:
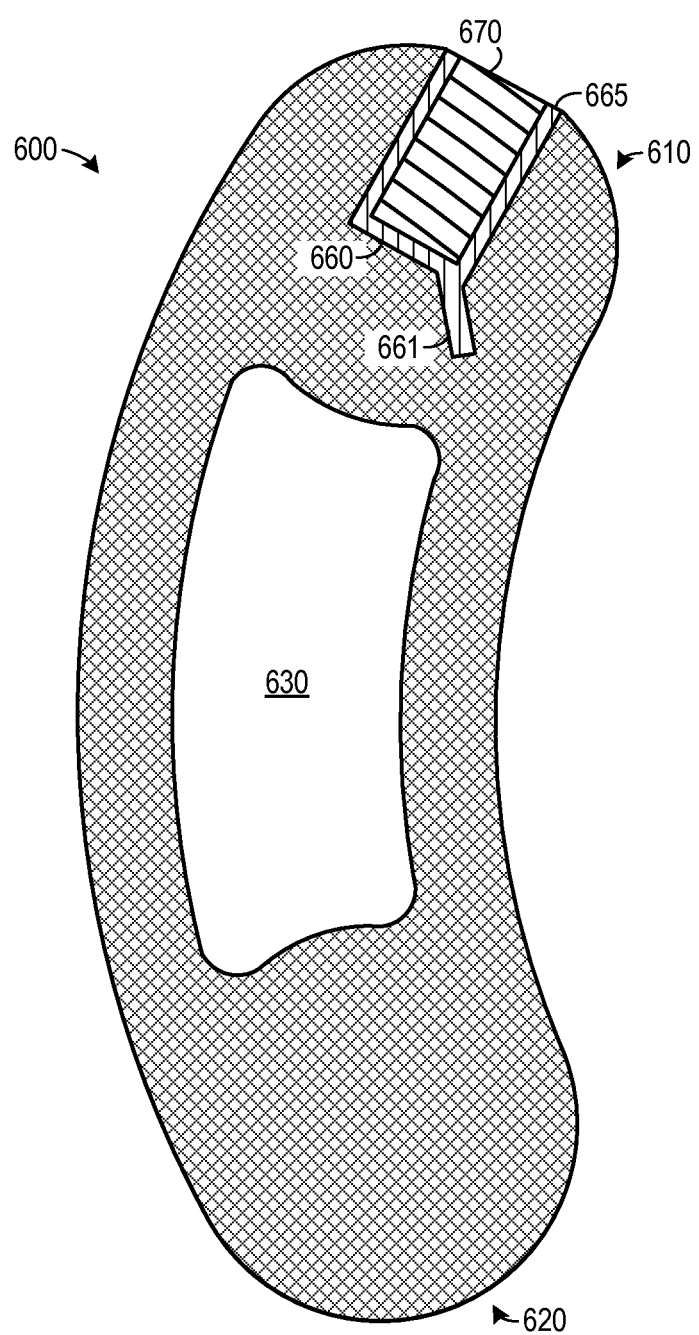
FIG. 6A is a cross-sectional view of an exemplary non-threadable interbody spacer with threads formed in a threadable material inserted within a cavity in a proximal end of the interbody spacer, the cavity including an anti-rotational feature.

FIG. 6A is a cross-sectional view of another embodiment of a non-threadable interbody spacer 600 with threads 670 formed in an insert of threadable material 665 inserted within a cavity 660 in a proximal end 610 of the interbody spacer 600. As illustrated, cavity 660 may include an anti-rotational and/or retention forming cavity to form an anti-rotational and/or retention member 661. Threadable material 665 may be inserted within the anti-rotational and/or retention forming cavity. Accordingly, as rotational force is applied to threads 670 formed in threadable material 665, anti-rotational member 661 may prevent or reduce the likelihood that threadable material 665 will rotate within cavity 660 and also, or alternatively, may prevent or reduce the likelihood that the insert may be removed from the implant.

Figure 6B:
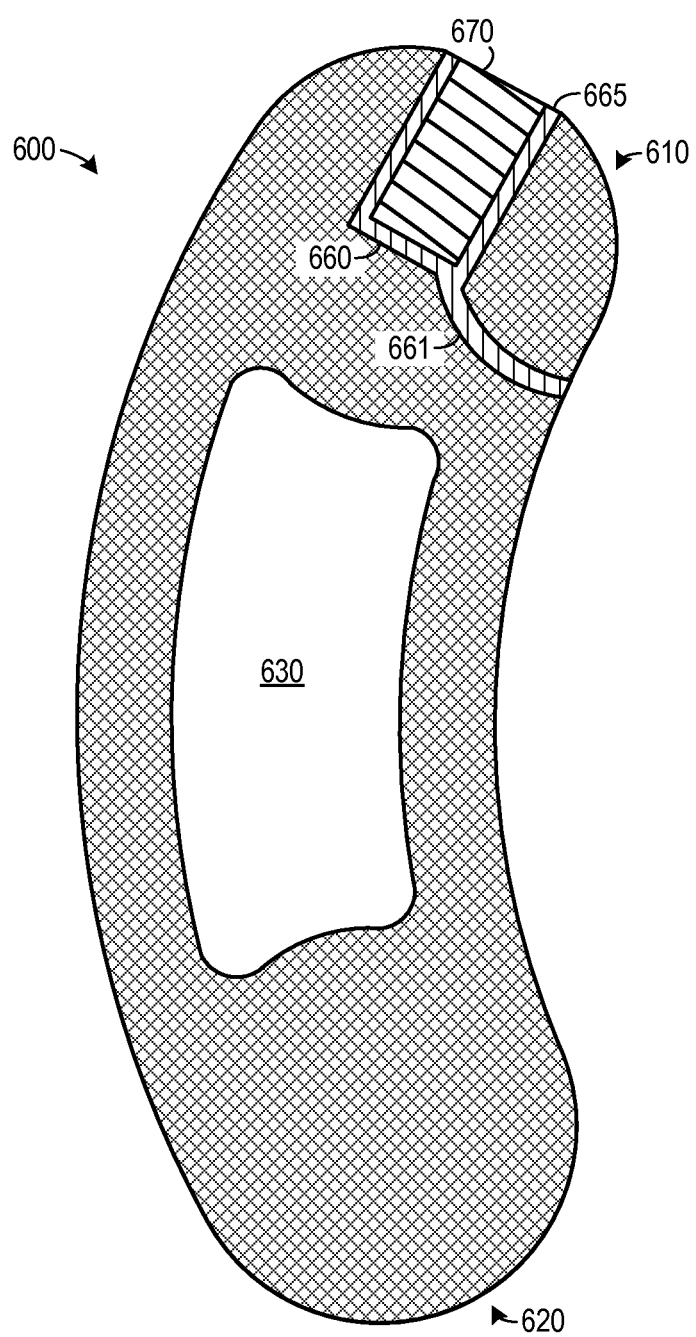
FIG. 6B is a cross-sectional view of an exemplary non-threadable interbody spacer with threads formed in a threadable material inserted within a cavity, the cavity including a vent.

FIG. 6B is a cross-sectional view of interbody spacer 600 with threads 670 formed in a threadable material 665 inserted within a cavity 660. In the illustrated embodiment, cavity 660 includes a vent 661 extending from cavity 660 to a side opening closer to distal end 620. Vent 661 may be any shape, diameter, or length. Vent 661 may allow air within cavity 660 to escape as threaded material 665 is inserted, thereby reducing the possibility and/or amount of gas that may be trapped within cavity 660. Additionally, vent 661 may be used to form an anti-rotation member to prevent threaded material 665 from rotating within cavity 660.

Again, aperture 630 may serve as a delivery mechanism for BMP and/or provide a location for additional bone growth. Interbody spacer 600 may comprise a non-threadable silicon nitride or other ceramic, glass, and/or other material. Threadable material 665 may comprise PEEK, polypropylene, titanium, aluminum, other metal, an alloy, an epoxy, and/or other material capable of being threaded.

Figure 6C:
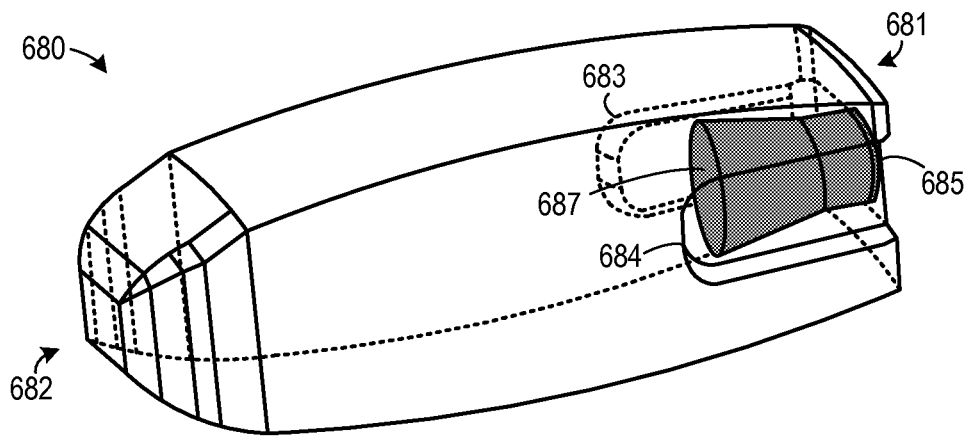
FIG. 6C is a perspective view of a threadable material inserted within a tapered cavity in a proximal end of a surgical implant.

FIG. 6C is a perspective view of an insert 685 positioned within a tapered cavity 687 in a proximal end 681 of a surgical implant 680. Insert 685 may be made up of a threadable material. According to various embodiments, surgical implant 680 may include a tapered distal end 682 and one or more engagement features 683 and 684. The opening of tapered cavity 687 may be located on proximal end 681 of surgical implant 680. As illustrated, the base of tapered cavity 687 may be wider than the opening of tapered cavity 687. Tapered cavity 687 may provide an advantage in that threadable material 685 cannot be easily removed from tapered cavity 687 once threadable material 685 has solidified or otherwise become secured within tapered cavity 687.

According to various embodiments, threadable material 685 may be melted, press-fit, or injected within tapered cavity 687. Threadable material 685 may comprise PEEK, polypropylene, titanium, aluminum, other metal, an alloy, an epoxy, and/or other material capable of being threaded. The wider distal end of tapered cavity 687 may prevent the removal of threadable material 685. In some embodiments, one or more anti-rotational features may also be provided to prevent or at least reduce the likelihood that the insert 685 will rotate within tapered cavity 687.

Figure 6D:
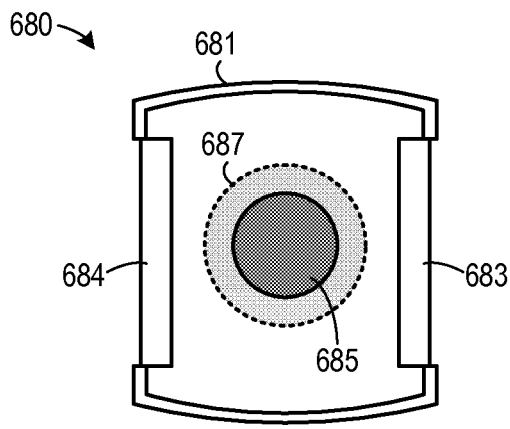
FIG. 6D is a view of the proximal end of the surgical implant, including the threadable material inserted within the tapered cavity.

FIG. 6D is a view of the proximal end 681 of the surgical implant 680, including insert 685 positioned within tapered cavity 687. Threadable material 685 in the distal end of tapered cavity 687 is larger than the proximal opening of tapered cavity 687. Accordingly, threadable material 685 cannot be pulled from tapered cavity 687 once it has been fully secured within tapered cavity 687.

Figure 6E:
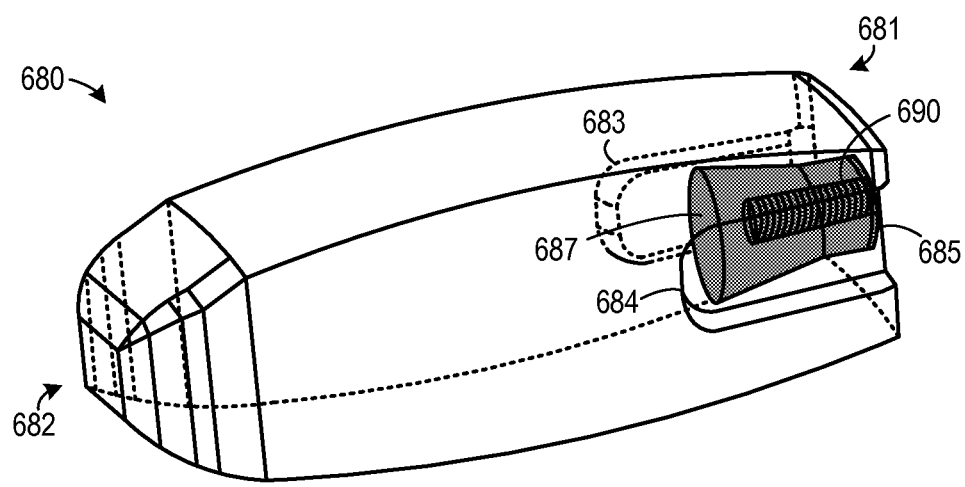
FIG. 6E is a phantom view of the surgical implant with threads formed within the threadable material inserted within the tapered cavity.

FIG. 6E is a perspective, phantom view of surgical implant 680. As shown in this figure, insert 685 is positioned within tapered cavity 687 and may comprise threads 690 in order so as to form a female-threaded insert within tapered cavity 687. Any of a wide variety of insertion tools and/or fasteners may then be threadably secured to female-threaded insert 685. For example, an insertion tool may threadably secure surgical implant 680 during insertion, removal, or manipulation via female-threaded insert 685.

Figure 7A:
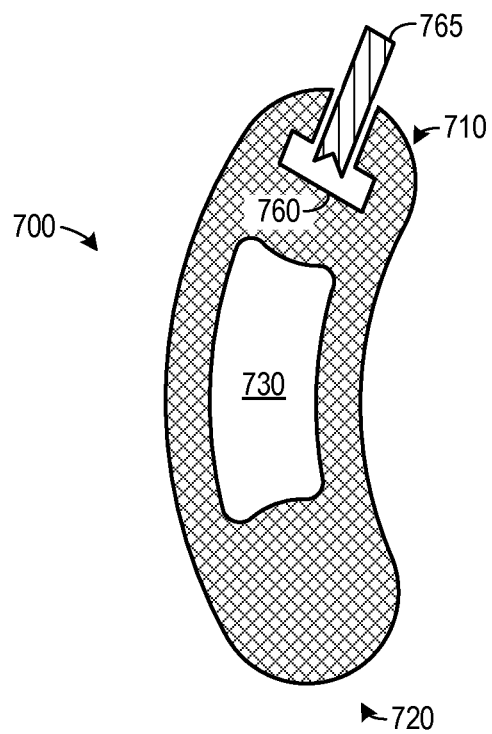
FIG. 7A is a cross-sectional view of an exemplary non-threadable interbody spacer with a threadable material ready to be press-fit within a wide-base cavity in a proximal end of the interbody spacer.
Figure 7B:
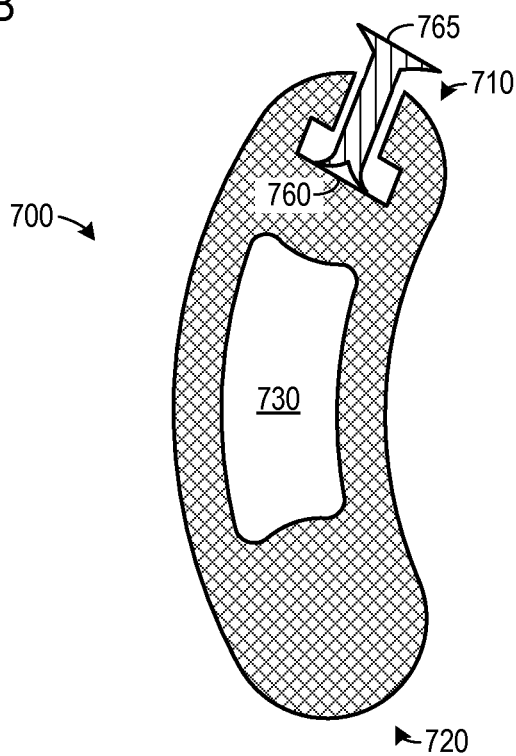
FIG. 7B is a cross-sectional view of the non-threadable interbody spacer with the threadable material being press-fit within the wide-based cavity.

FIG. 7A is a cross-sectional view of a non-threadable interbody spacer 700 including a proximal end 710, a distal end 720, and an aperture 730. Interbody spacer 700 may include a wide-base cavity 760 configured with a wider base than opening. According to one embodiment, a threadable material 765 may be press-fit within a wide-base cavity in a proximal end 710 of the interbody spacer 700. As illustrated, threadable material 76 may be configured with a V shaped nose configured to split and fill the wide base of cavity 760 as it is press-fit. Threadable material 765 may be heated in order to increase malleability a facilitate expansion of threadable material 765 throughout the confines of cavity 760. As illustrated in FIG. 7B, threadable material 765 may be malleable, such that as it is press fit within cavity 760, the V-shaped nose fills the wide base of cavity 760. Threadable material 765 may also, or additionally, be heated in order to increase malleability. According to some embodiments, press-fitting a relatively malleable threadable material 765, such as PEEK or titanium, may result in some deformation (mushrooming) of the top surface 767 above cavity 760, as illustrated in FIG. 7C.

Figure 7C:
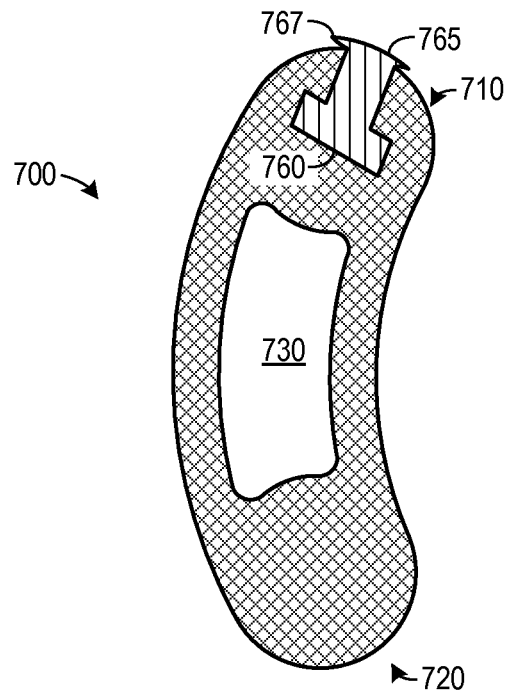
FIG. 7C is a cross-sectional view of the non-threadable interbody spacer with the threadable material press-fit within the wide-based cavity.

FIG. 7C provides a cross-sectional view of the non-threadable interbody spacer 700 with the threadable material 765 press-fit within cavity 760. As illustrated, the V-shaped nose of threadable material 765 may facilitate filling cavity 760. Again, as the relatively malleable threadable material 765 is press-fit, it may deform and/or mushroom along a top surface 767. The mushroomed top surface 767 may be sanded or otherwise removed until top surface 765 is even with the exterior surface of the spacer 700.

Figure 7D:
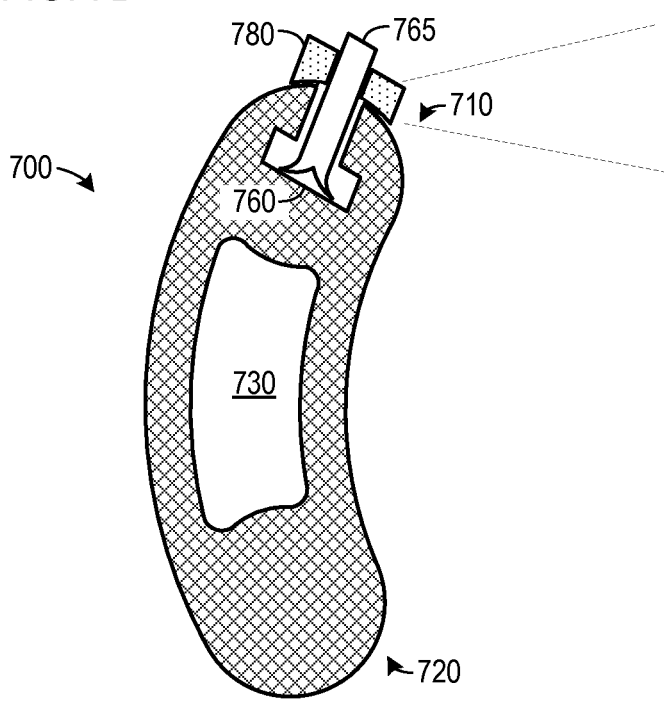
FIG. 7D is a cross-sectional view of the non-threadable interbody spacer with the threadable material being press-fit within the wide-based cavity using a ring configured to prevent mushrooming.
Figure 7E:
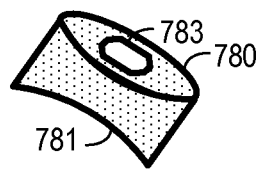
FIG. 7E is a perspective view of a ring configured to reduce or prevent mushrooming of a threadable material as it is press-fit within a cavity in an interbody spacer.

According to one embodiment, to reduce the mushrooming and deformation effects of press-fitting a malleable threadable material, a guide structure may be used to guide the malleable threadable material as it is press-fit within a cavity. FIG. 7D illustrates a cross-section view of an embodiment including a guide structure 780 formed as a ring. FIG. 7E illustrates a perspective view of such a ring for use in conjunction with the spacer shown in FIG. 7D. Guide structure 780 may include an engagement surface 781 configured with a shape corresponding to proximal end 710 of interbody spacer 700. The shape of engagement surface 781 may vary depending on the desired location of the insert and/or the shape and size of the spacer. The height and diameter of center hole 783 may vary based on the height of the threadable material to be press-fit and/or the size and shape of the cavity 760.

As illustrated, malleable threadable material 765 may be press-fit into cavity 760 using guide structure 780 to prevent or reduce deformation and/or mushrooming of the top surface. Moreover, the diameter of center hole 783 may be configured so as to maximize the flow of threadable material 765 based on the type of material used and its characteristics, such as malleability, temperature, viscosity, etc.

Figure 8A:
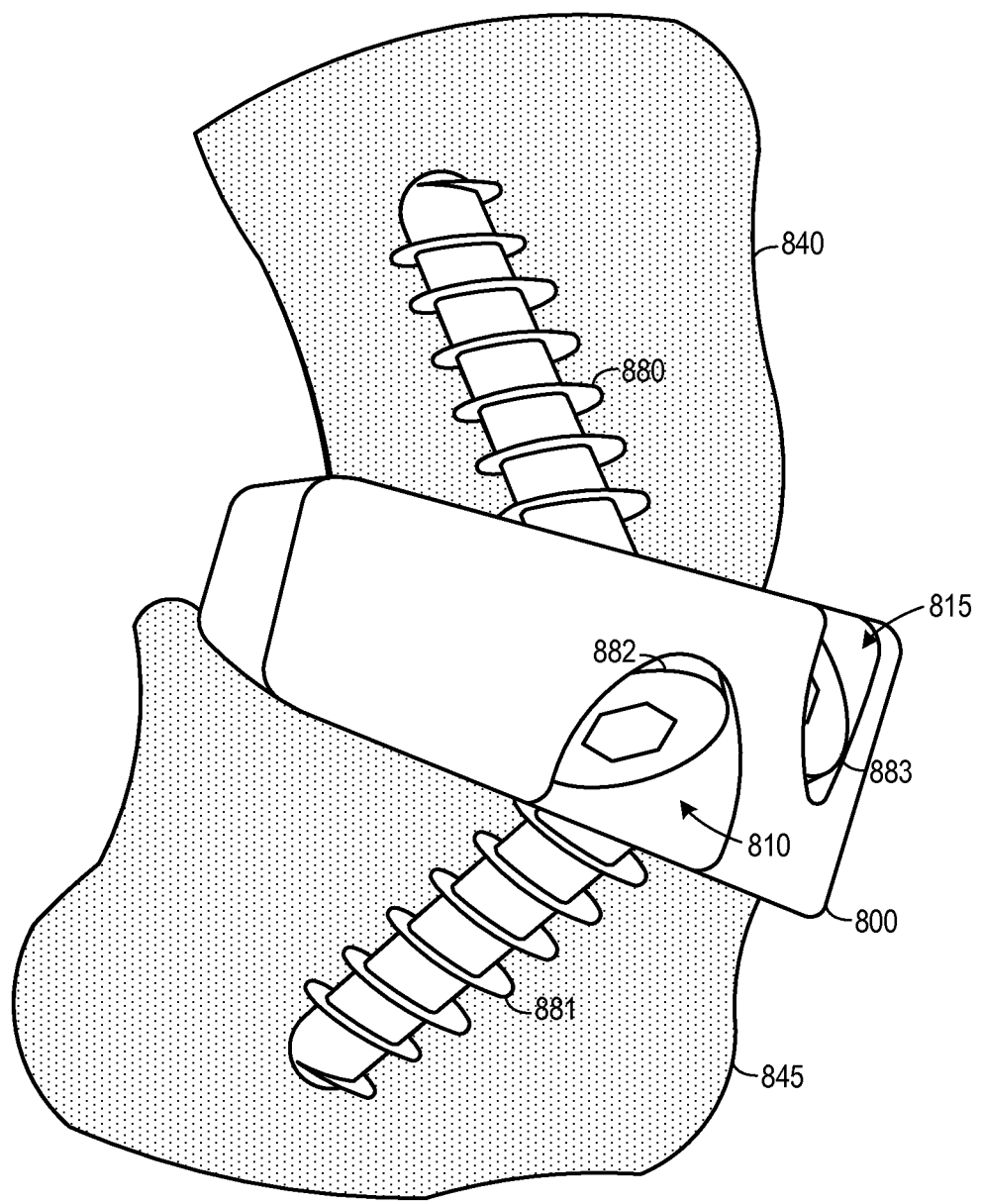
FIG. 8A is a perspective view of a non-threadable interbody spacer, including multiple female-threaded insert configured to each receive a bone screw for use in a standalone anterior lumbar interbody fusion (STALIF) implant.

FIG. 8A is a perspective view of a non-threadable interbody spacer 800, including multiple female-threaded inserts (not shown in this figure). The female-threaded inserts may comprise female-threaded thru-bores configured to threadably receive bone screw 880 and bone screw 881. As illustrated, interbody spacer 800 may be positioned between upper vertebrae 840 and lower vertebrae 845. Bone screws 880 and 881 may be configured to threadably pass through the female-threaded inserts and into upper and lower vertebrae 840 and 845. Any number of female-threaded inserts may be formed at various angles within an interbody spacer for use in a STALIF configuration. Interbody spacer 800 may include recesses 810 and 815 to accommodate the heads 882 and 883 of bone screws 880 and 881, respectively.

According to various embodiments, interbody spacer 800 may include any number of female-threaded inserts in order to provide sufficient support via a corresponding number of bone screws for a STALIF configuration. For example, in one embodiment, interbody spacer 800 may include two female-threaded inserts angled in an upward direction and two female-threaded inserts angled in a downward direction.

A STALIF configuration utilizing such an interbody spacer may include four bone screws, two entering the upper vertebrae 840 and two entering the lower vertebrae 845.

Figure 8B:
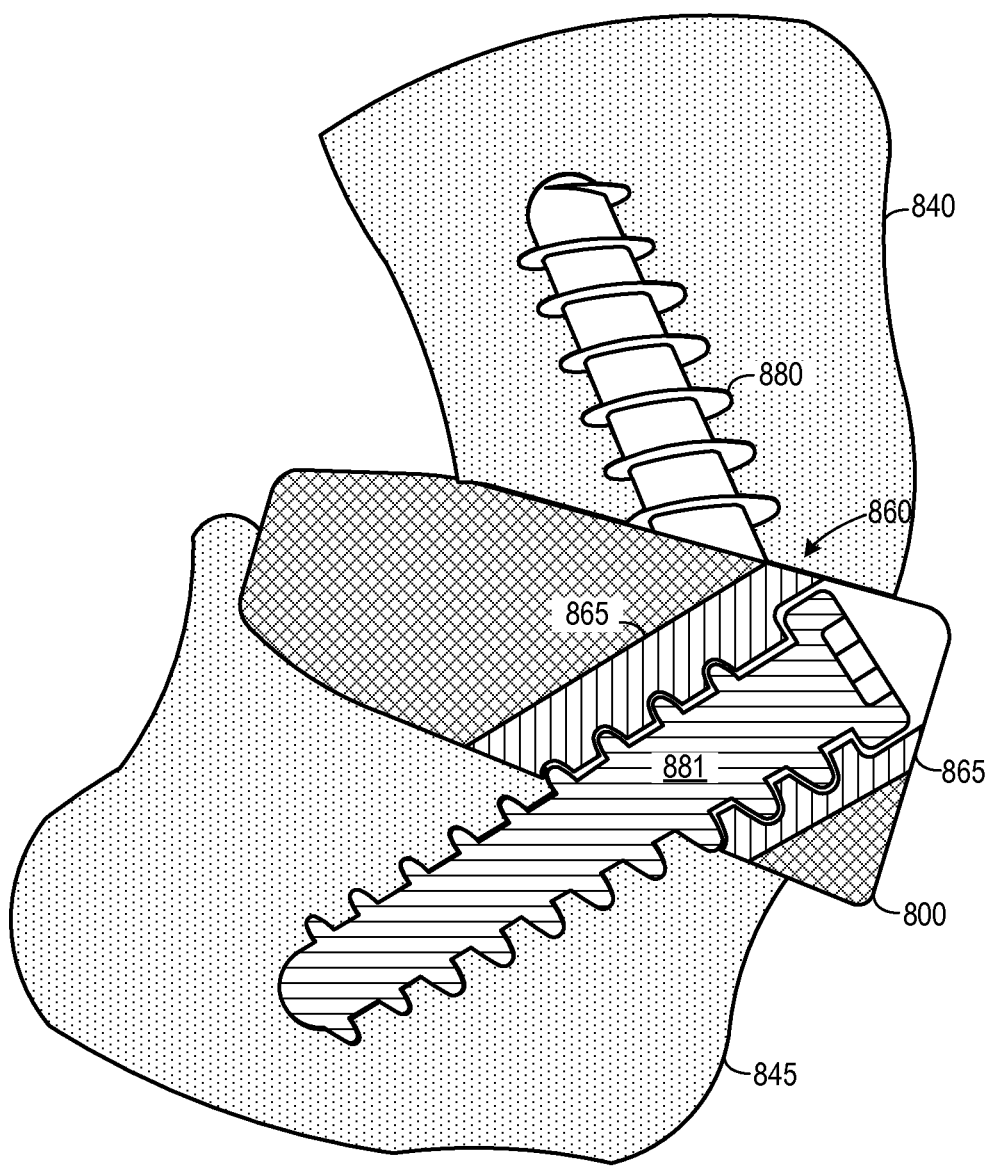
FIG. 8B is a cut-away view of the non-threadable interbody spacer, including the female-threaded inserts receiving bone screws in a STALIF configuration.

FIG. 8B is a cut-away view of non-threadable interbody spacer 800, including a female-threaded insert 860 receiving a bone screw 881 in a STALIF configuration. Bone screw 881 may be configured to threadably pass through interbody spacer 800 and into lower vertebrae 845. Female-threadable insert 860 may be formed by creating a thru-bore in interbody spacer 800. The thru-bore may be filled with a threadable material 865. Threadable material 865 may then be threaded in order to form a female-threaded insert 860 passing through interbody spacer 800. In such embodiments, the female-threaded insert 860 is a female-threaded thru-bore passing through interbody spacer 800. In other embodiments, the opening within which the insert is installed need not comprise a thru-bore.

Similar to previous embodiments, threadable material 865 may comprise PEEK or other threadable material, and interbody spacer may be manufactured using a non-threadable material, such as silicon nitride or another ceramic material.

Figure 8C:
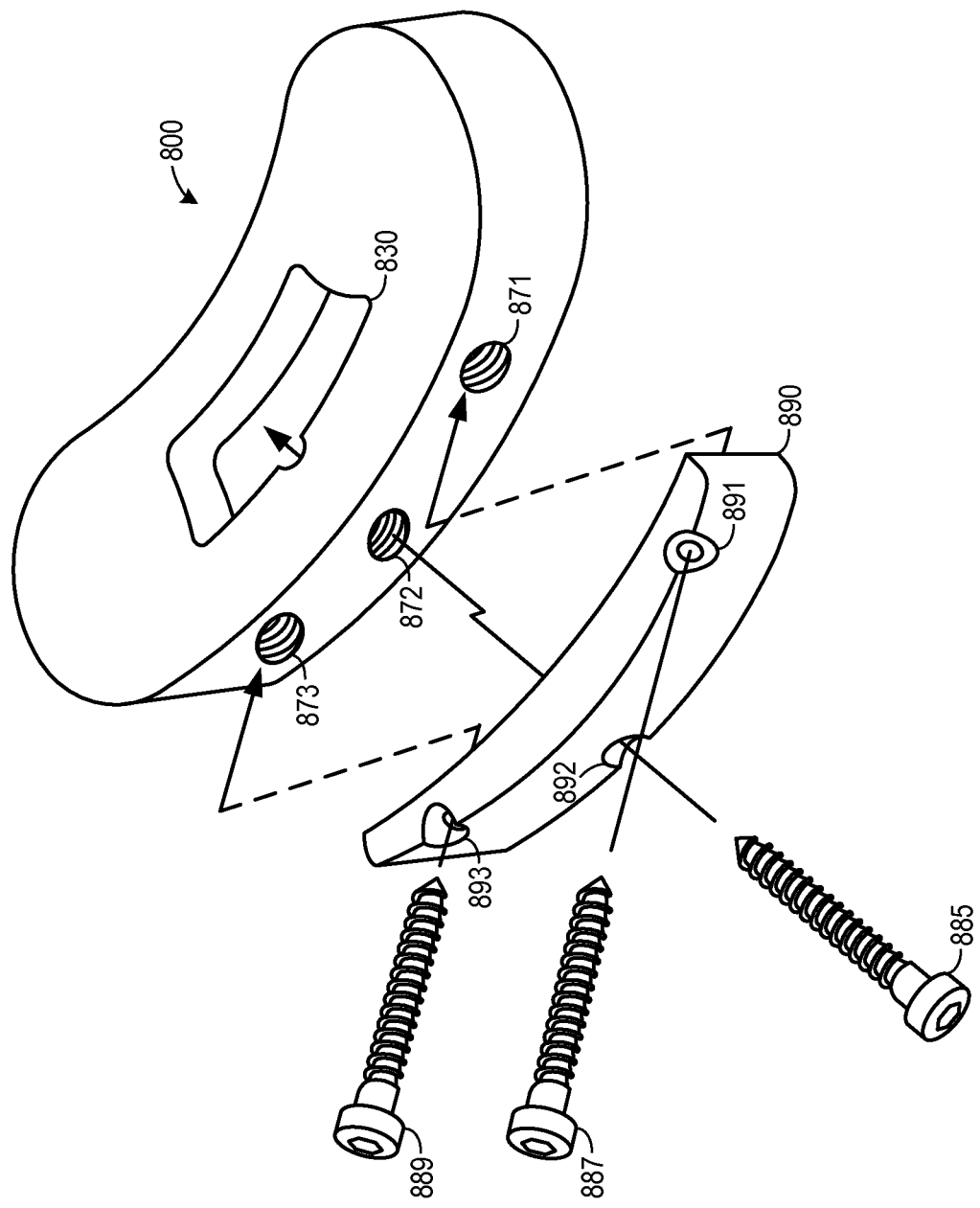
FIG. 8C is a perspective view of a bone screw plate and a non-threadable interbody spacer, including a plurality of female-threaded inserts configured to receive bone screws for use in a STALIF configuration.

FIG. 8C is a perspective view of a plate 890 and a non-threadable interbody spacer 800, including a plurality of female-threaded inserts 871-873. Each female-threaded insert 871-873 may be configured to receive a bone screw 885, 887, and 889 at an angle, such as for use in a STALIF configuration. As illustrated, female-threaded inserts 871 and 873 are configured to threadably receive bone screws 887 and 889, respectively. Bone screws 887 and 889 may be threaded through female-threaded inserts 871 and 873 at a downward angle into a lower vertebra.

Female-threaded insert 872 may be configured to threadably receive bone screw 885 at an upward angle, such that bone screw 885 enters an upper vertebra after passing through interbody spacer 800. Plate 890 may serve as an intermediary between the heads of bone screws 885-889 and the surface of interbody spacer 800. As illustrated, bone screws 885, 887, and 889 may pass through apertures 891, 892, and 893 in bone screw plate 890, through female-threaded inserts 871, 872, and 873, and into the adjacent vertebrae. According to some embodiments, apertures 891-893 may be threaded. Alternatively, apertures 891-893 may not be threaded, allowing the shafts of bone screws 885-889 to slidably pass therethrough while retaining the heads of bone screws 885-889.

As previously described, some material types used to manufacture non-threadable interbody spacers, such as interbody spacer 800, may not support point loads without the risk of fracturing. Thus, without plate 890, the heads of bone screws 885-889 may exert a point load on the surface of interbody spacer 800 sufficient to fracture, or otherwise damage, interbody spacer 800. Accordingly, bone screw plate 890 may serve as an intermediary between the heads of bone screws 885-889 and the surface of interbody spacer 800. Plate 890 may distribute the force from the heads of bone screws 885-889 across the face of interbody spacer 800.

According to various embodiments, plate 890 may comprise a metal, such as titanium or aluminum. Alternatively, plate 890 may comprise PEEK, a ceramic capable of distributing the point loads from the heads of bone screws 885-889, an alloy, a plastic, and/or any other suitable material.

Figure 9A:
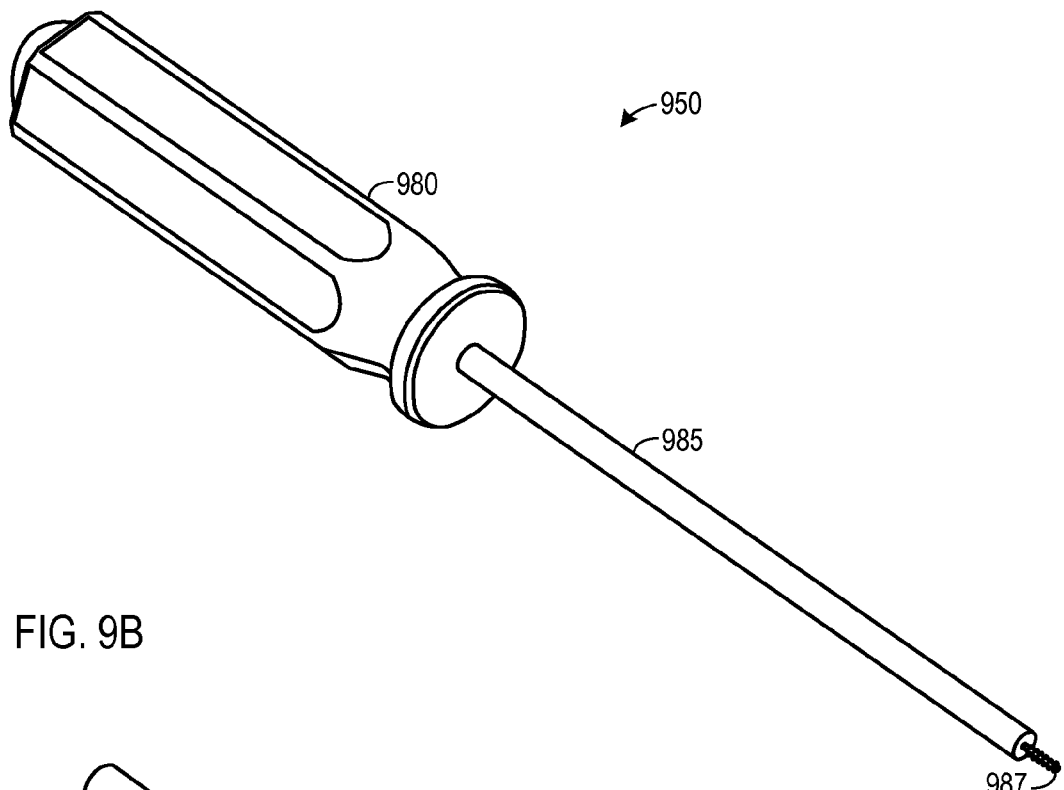
FIG. 9A is a perspective view of an exemplary insertion tool, including a male-threaded tip adapted to threadably secure a female-threaded insert formed within an interbody spacer.

FIG. 9A is a perspective view of an exemplary insertion tool 950, including a handle 980, an extension 985, and a male-threaded tip 987. According to various embodiments, male-threaded tip 987 may be used to threadably secure an interbody spacer during surgical insertion. Male-threaded tip 987 may be adapted to accommodate any size or shape interbody spacer and/or female-threaded insert within an interbody spacer. According to some embodiments, insertion tool 950 may be configured to pivot an interbody spacer relative to extension 985 during insertion.

Figure 9B:
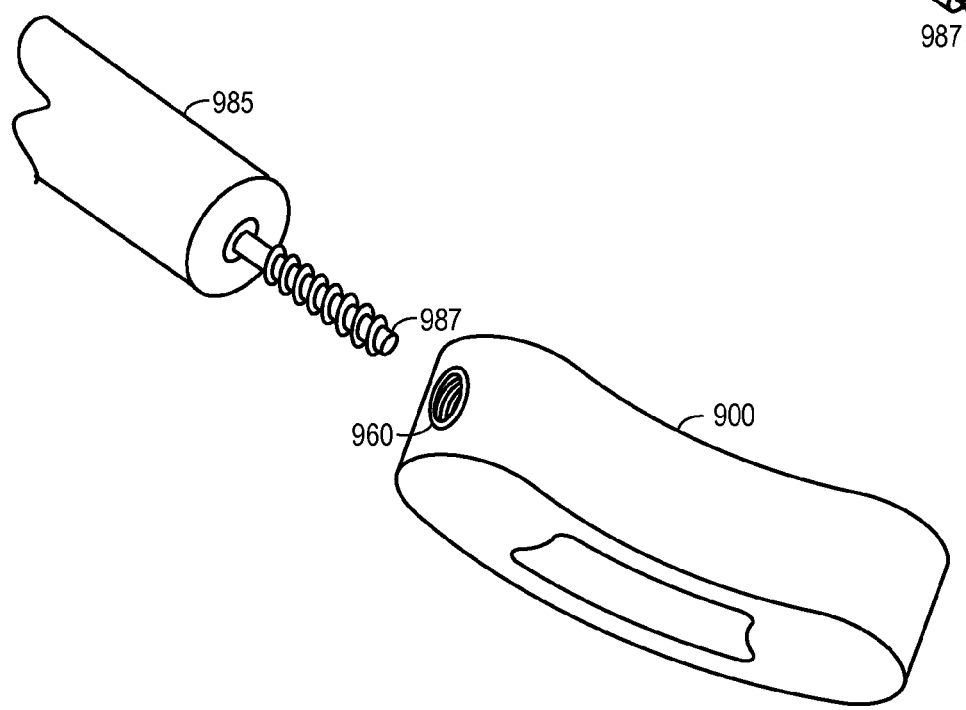
FIG. 9B is a perspective view of a close-up of the male-threaded tip of the insertion tool engaging the female-threaded insert formed in an exemplary interbody spacer.

FIG. 9B is a perspective view of a close-up of male-threaded tip 987 at the end of extension 985 of the insertion tool engaging a female-threaded insert 960 formed on a proximal end of an interbody spacer 900. Female-threaded insert 960 is illustrated as a circular insert; however, the shape of female-threaded insert 960 may be any shape, including rectangular, hexagonal, octagonal, oval, and/or other non-round shapes. Moreover, although not visible in the perspective view of FIG. 9B, the cavity within which female-threaded insert 960 is formed may be tapered, may include a wider base than entrance, may include an anti-rotational feature, may include a vent, and/or may be of any shape, size, or depth.

Figure 10:
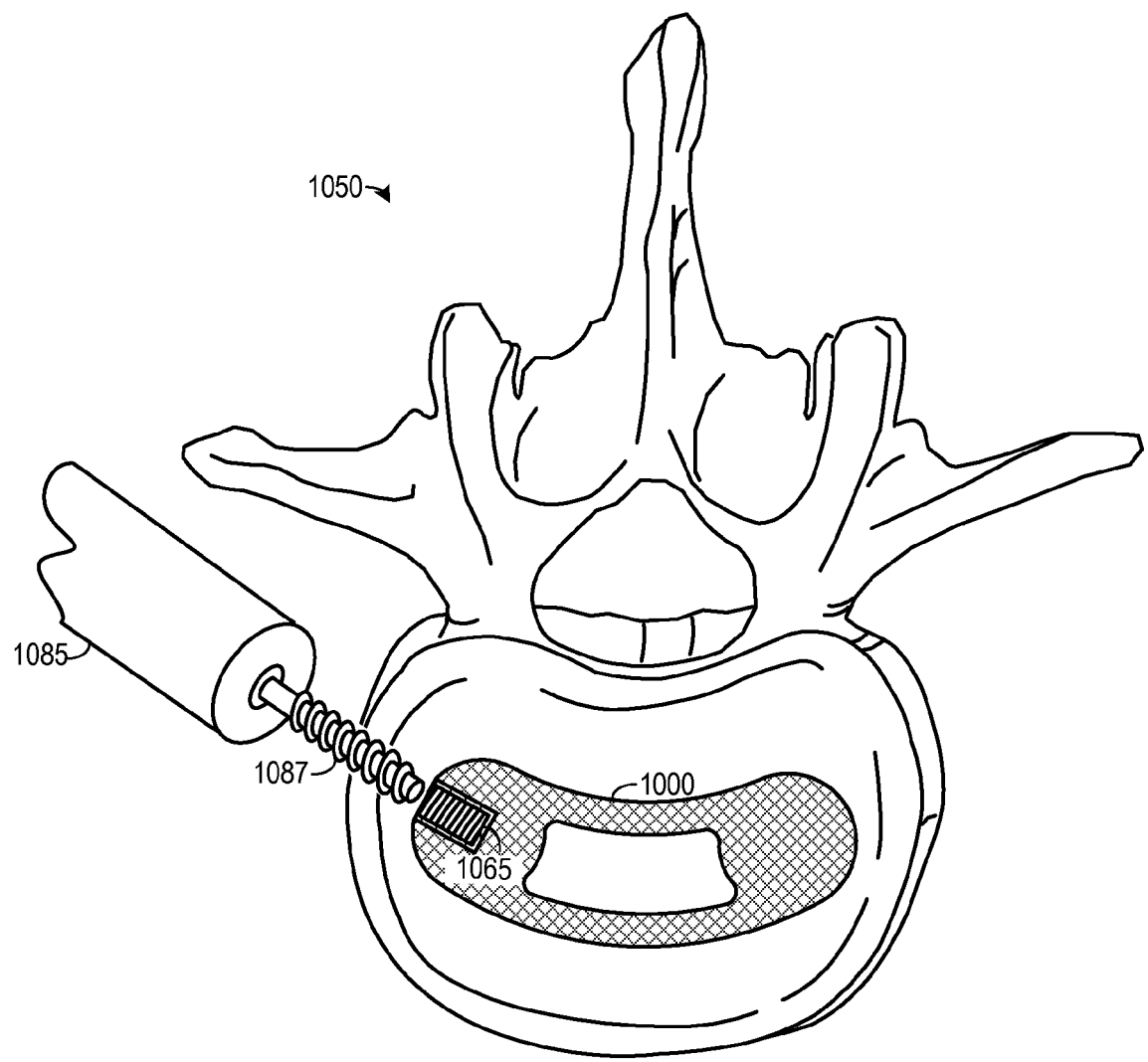
FIG. 10 is a perspective view of an insertion tool engaging an intervertebral spacer in place within a spinal region.

FIG. 10 is a perspective view of a male-threaded tip 1087 of an insertion tool 1085 engaging a female-threaded insert 1065 formed in a proximal end of an intervertebral spacer 1000 within a spinal region 1050. According to various embodiments, intervertebral spacer 1000 may be inserted or removed from the spinal region 1050 using any of a wide variety of surgical techniques, such as PLIF and TLIF approaches. Again, the shape of female-threaded insert 1065 may be round, rectangular, hexagonal, octagonal, oval, n-polygonal, or other shape. Moreover, the cavity within which female-threaded insert 1065 is formed may be tapered, include a wider base than entrance, include an anti-rotational and/or retention feature, include a vent, and/or have any shape, size, or depth.

FIG. 11 is a flow chart of one method 1100 for forming a female-threaded insert within a proximal end of an interbody spacer. A cavity is formed in a non-threadable interbody spacer, at 1110. According to various embodiments, the interbody spacer may comprise a glass, silicon nitride or another ceramic material, or a porous material. The cavity may be formed using a process such as mechanical drilling, chemical etching, laser etching, particle blasting, and/or other cavity-forming process. Alternatively, a cavity may be formed in an interbody spacer during the manufacturing of the interbody spacer, such as through the use of molds configured to provide a cavity.

A threadable material, or a material having desired properties that may be lacking in the spacer itself, may then be inserted into the cavity at 1120. The threadable material inserted into the cavity may comprise PEEK (polyehtere-therketone), polypropylene, titanium, a metal, an alloy, and/or other material capable of being threaded. The threadable material may be inserted within the cavity using any of a wide variety of insertion processes, including, but not limited to, press-fitting, injection molding, extrusion, adhesives, or melting. According to some embodiments, a combination of insertion processes may be utilized. For example, a PEEK material may be injected into the cavity and then pressed within the cavity to finalize the insertion.

The threadable material may then be threaded at 1130. Threading the threadable material forms a female-threaded insert within the cavity of the interbody spacer. A male-threaded tip of an insertion tool may then be threadably attached to the female-threaded insert within the cavity at 1140. The insertion tool may then securely manipulate the interbody spacer via the female-threaded insert during a surgical procedure at 1150.

Of course, the steps in the 1100 need not be performed in the order depicted in FIG. 11 in all implementations. For example, the insert may be threaded before the insert is placed within the implant.

The foregoing specification has been described with reference to various embodiments. However, one of ordinary skill in the art will appreciate that various modifications and changes can be made without departing from the scope of the present disclosure. For example, various operational steps, as well as components for carrying out operational steps, may be implemented in alternate ways depending upon the particular application or in consideration of any number of cost functions associated with the operation of the system. Accordingly, any one or more of the steps may be deleted, modified, or combined with other steps. Further, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced, are not to be construed as a critical, a required, or an essential feature or element.

Those having skill in the art will appreciate that many changes may be made to the details of the above-described embodiments without departing from the underlying principles of the invention. The scope of the present invention should, therefore, be determined only by the following claims.

The invention claimed is:

1. A method for forming a connectable insert within a biomedical implant, the method comprising the steps of:
   providing an implant body comprising a first material, wherein the first material is non-threadable;
   forming a wide-base cavity in the implant body, wherein the wide-base cavity is configured to prevent the insert from being removed from the cavity, wherein the wide-base cavity comprises a base at a first end of the wide-base cavity, wherein the wide-base cavity comprises an opening at a second end of the wide-base cavity, and wherein the base is wider than the opening;
   positioning an insert within the cavity, wherein the insert comprises a second material distinct from the first material, wherein the second material has physical properties distinct from the first material, and wherein the step of positioning an insert within the cavity is performed after the step of forming a wide-base cavity; and
   forming a female thread within the insert.

2. The method of claim 1, wherein the implant body comprises a spinal spacer.

3. The method of claim 2, wherein the spinal spacer comprises a concave face and an opposite convex face, and wherein the spinal spacer further comprises a first end wall connecting the concave face with the convex face and an opposite second end wall connecting the concave face with the convex face.

4. The method of claim 3, wherein the cavity is positioned within at least one of the first and second end walls.

5. The method of claim 1, wherein the step of positioning an insert within the cavity comprises at least one of press-fitting, injection molding, extruding, and melting the second material into the cavity.

6. The method of claim 1, further comprising forming an anti-rotation feature on the insert.

7. The method of claim 6, wherein the step of forming an anti-rotation feature on the insert comprises forming an anti-rotation cavity that is coupled with the cavity.

8. The method of claim 1, wherein the step of positioning an insert within the cavity comprises:
   providing a block of threadable material having a V-shaped nose; and
   forcing the block of threadable material into the cavity such that the V-shaped nose enters the cavity first.

9. The method of claim 1, wherein the step of positioning an insert within the cavity comprises heating the second material in order to increase the malleability of the second material.

10. The method of claim 1, wherein the step of positioning an insert within the cavity comprises:
    providing a guide structure comprising a center hole and an engagement surface configured with a shape corresponding to a surface of the implant body surrounding the cavity; and
    pressing the second material into the cavity through the guide structure.

11. The method of claim 1, wherein the opening of the wide-base cavity is formed at a proximal end of the wide-base cavity.

12. The method of claim 11, wherein the base of the wide-base cavity is formed at a distal portion of the wide-base cavity.

13. The method of claim 12, wherein the base of the wide-base cavity is formed at a distal-most end of the wide-base cavity.

* * * * *